United States Patent [19]

Giordano

[11] Patent Number: 5,674,748
[45] Date of Patent: Oct. 7, 1997

[54] HUMAN CYCLIN-DEPENDENT KINASE-LIKE PROTEINS AND METHODS OF USING THE SAME

[75] Inventor: Antonio Giordano, Philadelphia, Pa.

[73] Assignee: Thomas Jefferson University, Philadelphia, Pa.

[21] Appl. No.: 403,634

[22] Filed: Mar. 14, 1995

[51] Int. Cl.$^6$ .............................. C12N 1/21; C12N 5/10; C12N 15/54; C12N 15/63
[52] U.S. Cl. ................. 435/325; 435/252.3; 435/254.11; 435/320.1; 536/23.2; 536/24.31
[58] Field of Search ........................ 435/320.1, 240.2, 435/252.3, 254.11; 536/23.2, 24.31

[56] References Cited

U.S. PATENT DOCUMENTS

| | | | |
|---|---|---|---|
| 4,736,866 | 4/1988 | Leder et al. | 800/2 |
| 4,873,191 | 10/1989 | Wagner et al. | 435/172.3 |
| 5,108,921 | 4/1992 | Low et al. | 435/375 |
| 5,294,538 | 3/1994 | Beach | 435/21 |

OTHER PUBLICATIONS

Kimura et al., Nature 356:526–529.
Claudio, P.P. et al., "p130/pRb2 has growth suppressive properties similar to yet distinctive from those of retinoblastoma family members pRb and p107", Cancer Research 1994, 54, 5556–5560.
Cropp, C.S. et al., "Identification of three regions on chromosome 17q in primary human breast carcinomas which are frequently deleted", Cancer Research 1993, 53, 5617–5619.
Futreal, P.A. et al., "Mutation analysis of the THRA1 gene in breast cancer: deletion/fusion of the gene to a novel sequence on 17q in the BT474 cell line", Cancer Research 1994, 54 1791–1794.
Graña, X. et al., "PITALRE, a nuclear CDC2–related protein kinase that phosphorylates the retionoblastoma protein in vitro", Proc. Natl. Acad. Sci. USA 1994, 91, 3834–3838.
Graña, X. et al., "PISSLRE, a human novel CDC2–related protein kinase", Oncogene 1994, 9, 2097–2103.
Huebner, K. et al., "Twenty–seven nonoverlapping zinc finger cDNAs from human T cells map to nine different chromosomes with apparent clustering", Am. J. Hum. Genet. 1991, 48, 726–740.
Huebner, K. et al., "Chromosomal localization of four human zinc finger cDNAs", Hum. Genet 1993, 91 217–222.
LaForgia, S. et al., "Receptor protein–tyrosine phosphatase τ is a candidate tumor suppressor gene at human chromosome region 3p21", Proc. Natl. Acad. Sci. USA 1991, 88, 5036–5040.
Meyerson, M. et al., "A family of human cdc2–related protein kinases", EMBO Journal 1992, 11(8), 2909–2917.
Miki, Y. et al., "A strong candidate for the breast and ovarian cancer susceptibility gene BRCA1", Science 1994, 266, 66–71.

(List continued on next page.)

Primary Examiner—Eric Grimes
Attorney, Agent, or Firm—Woodcock Washburn Kurtz Mackiewicz & Norris LLP

[57] ABSTRACT

Substantially pure human cyclin-dependent kinase-like proteins PITALRE and PISSLRE and isolated protein complexes that comprise PITALRE or PISSLRE are disclosed. Isolated nucleic acid molecule that encode PITALRE or PISSLRE, or a fragment thereof; recombinant expression vectors that comprise nucleic acid sequences that encode PITALRE or PISSLRE; and host cells that comprise such recombinant expression vectors are disclosed. Oligonucleotide molecules that consist of a nucleotide sequence complementary to a portion of the nucleotide sequence that encodes PITALRE or PISSLRE are disclosed. Antibodies which bind to epitopes on PITALRE or PISSLRE are disclosed. Nucleic acid molecules that comprise a nucleotide sequence that encodes phosphorylation deficient PITALRE or a phosphorylation deficient PISSLRE; recombinant vectors and pharmaceutical compositions that comprise such nucleotide sequences are also disclosed. Methods of identifying compounds which inhibit PITALRE activity are disclosed.

11 Claims, 1 Drawing Sheet

OTHER PUBLICATIONS

Oliner, J.D. et al., "Amplification of a gene encoding a p53-associated protein in human sarcomas", *Nature* 1992, 358, 80-83.

Polyak, K. et al., "Cloning of p27$^{Kip1}$, a cyclin-dependent kinase inhibitor and a potential mediator of extracellular antimitogenic signals", *Cell* 1994, 78, 59-66.

Tsai, L. et al., "Isolation of the human cdk2 gene that encodes the cyclin A- and adenovirus E1A-associated p33 kinase", *Nature* 1991, 353, 174-177.

van der Heuvel, S. and Harlow, E., "Distinct roles for cyclin-dependent kinases in cell cycle control", *Science* 1993, 262, 2050-2054.

Xiong, Y. et al., "D type cyclins associate with multiple protein kinases and the DNA replication and repair factor PCNA", *Cell* 1992, 71, 505-514.

Zhu, L. et al., "Inhibition of cell proliferation by p107, a relative of the retinoblastoma protein", *Genes & Development* 1993, 7, 1111-1125.

Brambilla et al., Oncogene 9: 3037-3041 Oct. 1994.

Okuda et al., Oncogene 7:2249-2258 1992.

Liu et al., Amer. J. Pathol 146:228-238 Jan. 1995.

Auffray et al., Chem. Abstr. 123:307640f Dec. 1995.

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 1461 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 65..1180

( x i ) SEQUENCE DESCRIPTION: SEQ ID NO:1:

```
CGGGACCCGA GCAGGAGCGG CGGCACGAGC AGCTGGGGGC GGCGGCGGCG CGTTGGAGGC        60

GGCC ATG GCA AAG CAG TAC GAC TCG GTG GAG TGC CCT TTT TGT GAT GAA        109
     Met Ala Lys Gln Tyr Asp Ser Val Glu Cys Pro Phe Cys Asp Glu
     1               5                  10                  15

GTT TCC AAA TAC GAG AAG CTC GCC AAG ATC GGC CAA GGC ACC TTC GGG        157
Val Ser Lys Tyr Glu Lys Leu Ala Lys Ile Gly Gln Gly Thr Phe Gly
               20                  25                  30

GAG GTG TTC AAG GCC AGG CAC CGC AAG ACC GGC CAG AAG GTG GCT CTG        205
Glu Val Phe Lys Ala Arg His Arg Lys Thr Gly Gln Lys Val Ala Leu
           35                  40                  45
```

| | | | | | | | | | | | | | | | | |
|---|---|---|---|---|---|---|---|---|---|---|---|---|---|---|---|---|
| AAG | AAG | GTG | CTG | ATG | GAA | AAC | GAG | AAG | GAG | GGG | TTC | CCC | ATT | ACA | GCC | 253 |
| Lys | Lys | Val | Leu | Met | Glu | Asn | Glu | Lys | Glu | Gly | Phe | Pro | Ile | Thr | Ala | |
| | | 50 | | | | | 55 | | | | | 60 | | | | |
| TTG | CGG | GAG | ATC | AAG | ATC | CTT | CAG | CTT | CTA | AAA | CAC | GAG | AAT | GTG | GTC | 301 |
| Leu | Arg | Glu | Ile | Lys | Ile | Leu | Gln | Leu | Leu | Lys | His | Glu | Asn | Val | Val | |
| | 65 | | | | | 70 | | | | | 75 | | | | | |
| AAC | TTG | ATT | GAG | ATT | TGT | CGA | ACC | AAA | GCT | TCC | CCC | TAT | AAC | CGC | TGC | 349 |
| Asn | Leu | Ile | Glu | Ile | Cys | Arg | Thr | Lys | Ala | Ser | Pro | Tyr | Asn | Arg | Cys | |
| 80 | | | | | 85 | | | | | 90 | | | | | 95 | |
| AAG | GGT | AGT | ATA | TAC | CTG | GTG | TTC | GAC | TTC | TGC | GAG | CAT | GAC | CTT | GCT | 397 |
| Lys | Gly | Ser | Ile | Tyr | Leu | Val | Phe | Asp | Phe | Cys | Glu | His | Asp | Leu | Ala | |
| | | | | 100 | | | | | 105 | | | | | 110 | | |
| GGG | CTG | TTG | AGC | AAT | GTT | TTG | GTC | AAG | TTC | ACG | CTG | TCT | GAG | ATC | AAG | 445 |
| Gly | Leu | Leu | Ser | Asn | Val | Leu | Val | Lys | Phe | Thr | Leu | Ser | Glu | Ile | Lys | |
| | | | 115 | | | | | 120 | | | | | 125 | | | |
| AGG | GTG | ATG | CAG | ATG | CTG | CTT | AAC | GGC | CTC | TAC | TAC | ATC | CAC | AGA | AAC | 493 |
| Arg | Val | Met | Gln | Met | Leu | Leu | Asn | Gly | Leu | Tyr | Tyr | Ile | His | Arg | Asn | |
| | 130 | | | | | 135 | | | | | 140 | | | | | |
| AAG | ATC | CTG | CAT | AGG | GAC | ATG | AAG | GCT | GCT | AAT | GTG | CTT | ATC | ACT | CGT | 541 |
| Lys | Ile | Leu | His | Arg | Asp | Met | Lys | Ala | Ala | Asn | Val | Leu | Ile | Thr | Arg | |
| 145 | | | | | 150 | | | | | 155 | | | | | | |
| GAT | GGG | GTC | CTG | AAG | CTG | GCA | GAC | TTT | GGG | CTG | GCC | CGG | GCC | TTC | AGC | 589 |
| Asp | Gly | Val | Leu | Lys | Leu | Ala | Asp | Phe | Gly | Leu | Ala | Arg | Ala | Phe | Ser | |
| 160 | | | | 165 | | | | | 170 | | | | | 175 | | |
| CTG | GCC | AAG | AAC | AGC | CAG | CCC | AAC | CGC | TAC | ACC | AAC | CGT | GTG | GTG | ACA | 637 |
| Leu | Ala | Lys | Asn | Ser | Gln | Pro | Asn | Arg | Tyr | Thr | Asn | Arg | Val | Val | Thr | |
| | | | | 180 | | | | | 185 | | | | | 190 | | |
| CTC | TGG | TAC | CGG | CCC | CCG | GAG | CTG | TTG | CTC | GGG | GAG | CGG | GAC | TAC | GGC | 685 |
| Leu | Trp | Tyr | Arg | Pro | Pro | Glu | Leu | Leu | Leu | Gly | Glu | Arg | Asp | Tyr | Gly | |
| | | | 195 | | | | | 200 | | | | | 205 | | | |
| CCC | CCC | ATT | GAC | CTG | TGG | GGT | GCT | GGG | TGC | ATC | ATG | GCA | GAG | ATG | TGG | 733 |
| Pro | Pro | Ile | Asp | Leu | Trp | Gly | Ala | Gly | Cys | Ile | Met | Ala | Glu | Met | Trp | |
| | | 210 | | | | | 215 | | | | | 220 | | | | |
| ACC | CGC | AGC | CCC | ATC | ATG | CAG | GGC | AAC | ACG | GAG | CAG | CAC | CAA | CTC | GCC | 781 |
| Thr | Arg | Ser | Pro | Ile | Met | Gln | Gly | Asn | Thr | Glu | Gln | His | Gln | Leu | Ala | |
| | 225 | | | | | 230 | | | | | 235 | | | | | |
| CTC | ATC | AGT | CAG | CTC | TGC | GGC | TCC | ATC | ACC | CCT | GAG | GTG | TGG | CCA | AAC | 829 |
| Leu | Ile | Ser | Gln | Leu | Cys | Gly | Ser | Ile | Thr | Pro | Glu | Val | Trp | Pro | Asn | |
| 240 | | | | | 245 | | | | | 250 | | | | | 255 | |
| GTG | GAC | AAC | TAT | GAG | CTG | TAC | GAA | AAG | CTG | GAG | CTG | GTC | AAG | GGC | CAG | 877 |
| Val | Asp | Asn | Tyr | Glu | Leu | Tyr | Glu | Lys | Leu | Glu | Leu | Val | Lys | Gly | Gln | |
| | | | | 260 | | | | | 265 | | | | | 270 | | |
| AAG | CGG | AAG | GTG | AAG | GAC | AGG | CTG | AAG | GCC | TAT | GTG | CGT | GAC | CCA | TAC | 925 |
| Lys | Arg | Lys | Val | Lys | Asp | Arg | Leu | Lys | Ala | Tyr | Val | Arg | Asp | Pro | Tyr | |
| | | | 275 | | | | | 280 | | | | | 285 | | | |
| GCA | CTG | GAC | CTC | ATC | GAC | AAG | CTG | CTG | GTG | CTG | GAC | CCT | GCC | CAG | CGC | 973 |
| Ala | Leu | Asp | Leu | Ile | Asp | Lys | Leu | Leu | Val | Leu | Asp | Pro | Ala | Gln | Arg | |
| | | 290 | | | | | 295 | | | | | 300 | | | | |
| ATC | GAC | AGC | GAT | GAC | GCC | CTC | AAC | CAC | GAC | TTC | TTC | TGG | TCC | GAC | CCC | 1021 |
| Ile | Asp | Ser | Asp | Asp | Ala | Leu | Asn | His | Asp | Phe | Phe | Trp | Ser | Asp | Pro | |
| | | 305 | | | | | 310 | | | | | 315 | | | | |
| ATG | CCC | TCC | GAC | CTC | AAG | GGC | ATG | CTC | TCC | ACC | CAC | CTG | ACG | TCC | ATG | 1069 |
| Met | Pro | Ser | Asp | Leu | Lys | Gly | Met | Leu | Ser | Thr | His | Leu | Thr | Ser | Met | |
| 320 | | | | | 325 | | | | | 330 | | | | | 335 | |
| TTC | GAG | TAC | TTG | GCA | CCA | CCG | CGC | CGG | AAG | GGC | AGC | CAG | ATC | ACC | CAG | 1117 |
| Phe | Glu | Tyr | Leu | Ala | Pro | Pro | Arg | Arg | Lys | Gly | Ser | Gln | Ile | Thr | Gln | |
| | | | | 340 | | | | | 345 | | | | | 350 | | |
| CAG | TCC | ACC | AAC | CAG | AGT | CGC | AAT | CCC | GCC | ACC | ACC | AAC | CAG | ACG | GAG | 1165 |
| Gln | Ser | Thr | Asn | Gln | Ser | Arg | Asn | Pro | Ala | Thr | Thr | Asn | Gln | Thr | Glu | |
| | | | 355 | | | | | 360 | | | | | 365 | | | |

```
TTT GAG CGC GTC TTC TGAGGGCCGG CGCTTGCCAC TAGGGCTCTT GTGTTTTTT        1220
Phe Glu Arg Val Phe
        370

TCTTCTGCTA TGTGACTTGC ATCGTGGAGA CAGGGCATTT GAGTTTATAT CTCTCATGCA      1280

TATTTTATTT AATCCCCACC CTGGGCTCTG GGAGCAGCCC GCTGAGTGGA CTGGAGTGGA      1340

GCATTGGCTG AGAGACCAGG AGGGCACTGG AGCTGTCTTG TCCTTGCTGG TTTTCTGGAT      1400

GGTTCCCAGA GGGTTTCCAT GGGGTAGGAG GATGGGCTCG CCCACCAGTG ACTTTTCCC      1460

G                                                                      1461
```

( 2 ) INFORMATION FOR SEQ ID NO:2:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Lys Gln Tyr Asp Ser Val Glu Cys Pro Phe Cys Asp Glu Val
 1           5                  10                  15

Ser Lys Tyr Glu Lys Leu Ala Lys Ile Gly Gln Gly Thr Phe Gly Glu
            20                  25                  30

Val Phe Lys Ala Arg His Arg Lys Thr Gly Gln Lys Val Ala Leu Lys
        35                  40                  45

Lys Val Leu Met Glu Asn Glu Lys Glu Gly Phe Pro Ile Thr Ala Leu
 50                  55                  60

Arg Glu Ile Lys Ile Leu Gln Leu Leu Lys His Glu Asn Val Val Asn
 65                  70                  75                  80

Leu Ile Glu Ile Cys Arg Thr Lys Ala Ser Pro Tyr Asn Arg Cys Lys
                85                  90                  95

Gly Ser Ile Tyr Leu Val Phe Asp Phe Cys Glu His Asp Leu Ala Gly
            100                 105                 110

Leu Leu Ser Asn Val Leu Val Lys Phe Thr Leu Ser Glu Ile Lys Arg
        115                 120                 125

Val Met Gln Met Leu Leu Asn Gly Leu Tyr Tyr Ile His Arg Asn Lys
130                 135                 140

Ile Leu His Arg Asp Met Lys Ala Ala Asn Val Leu Ile Thr Arg Asp
145                 150                 155                 160

Gly Val Leu Lys Leu Ala Asp Phe Gly Leu Ala Arg Ala Phe Ser Leu
                165                 170                 175

Ala Lys Asn Ser Gln Pro Asn Arg Tyr Thr Asn Arg Val Val Thr Leu
            180                 185                 190

Trp Tyr Arg Pro Pro Glu Leu Leu Leu Gly Glu Arg Asp Tyr Gly Pro
        195                 200                 205

Pro Ile Asp Leu Trp Gly Ala Gly Cys Ile Met Ala Glu Met Trp Thr
210                 215                 220

Arg Ser Pro Ile Met Gln Gly Asn Thr Glu Gln His Gln Leu Ala Leu
225                 230                 235                 240

Ile Ser Gln Leu Cys Gly Ser Ile Thr Pro Glu Val Trp Pro Asn Val
                245                 250                 255

Asp Asn Tyr Glu Leu Tyr Glu Lys Leu Glu Leu Val Lys Gly Gln Lys
            260                 265                 270

Arg Lys Val Lys Asp Arg Leu Lys Ala Tyr Val Arg Asp Pro Tyr Ala
        275                 280                 285
```

| | | | | | | | | | | | | | | |
|---|---|---|---|---|---|---|---|---|---|---|---|---|---|---|
| Leu | Asp | Leu | Ile | Asp | Lys | Leu | Leu | Val | Leu | Asp | Pro | Ala | Gln | Arg | Ile |
| | 290 | | | | 295 | | | | | 300 | | | | |

| Asp | Ser | Asp | Asp | Ala | Leu | Asn | His | Asp | Phe | Phe | Trp | Ser | Asp | Pro | Met |
|---|---|---|---|---|---|---|---|---|---|---|---|---|---|---|---|
| 305 | | | | | 310 | | | | | 315 | | | | | 320 |

| Pro | Ser | Asp | Leu | Lys | Gly | Met | Leu | Ser | Thr | His | Leu | Thr | Ser | Met | Phe |
|---|---|---|---|---|---|---|---|---|---|---|---|---|---|---|---|
| | | | | 325 | | | | | 330 | | | | | 335 | |

| Glu | Tyr | Leu | Ala | Pro | Pro | Arg | Arg | Lys | Gly | Ser | Gln | Ile | Thr | Gln | Gln |
|---|---|---|---|---|---|---|---|---|---|---|---|---|---|---|---|
| | | | 340 | | | | | 345 | | | | | 350 | | |

| Ser | Thr | Asn | Gln | Ser | Arg | Asn | Pro | Ala | Thr | Thr | Asn | Gln | Thr | Glu | Phe |
|---|---|---|---|---|---|---|---|---|---|---|---|---|---|---|---|
| | | 355 | | | | | 360 | | | | | 365 | | | |

| Glu | Arg | Val | Phe |
|---|---|---|---|
| | | 370 | |

(2) INFORMATION FOR SEQ ID NO:3:

(i) SEQUENCE CHARACTERISTICS:
        (A) LENGTH: 1424 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 85..1032

(xi) SEQUENCE DESCRIPTION: SEQ ID NO:3:

| | | | | | | | | | |
|---|---|---|---|---|---|---|---|---|---|
| AGTCTGCGCC | TGCGCGCAAG | AGAGGCGGGG | CCAGCGCTCG | GCATGGCGGA | GCAGATCTGG | | | | 60 |

| AGTGCGAGCA | GATCCGTCTG | AAGT | GTA | TTC | CTG | GGA | CGA | TGC | CGG | AGT | GTG | 111 |
|---|---|---|---|---|---|---|---|---|---|---|---|---|
| | | | Val | Phe | Leu | Gly | Arg | Cys | Arg | Ser | Val | |
| | | | 1 | | | | 5 | | | | | |

| AAG | GAG | TTT | GAG | AAG | CTG | AAC | CGC | ATT | GGA | GAG | GGT | ACC | TAC | GGC | ATT | 159 |
|---|---|---|---|---|---|---|---|---|---|---|---|---|---|---|---|---|
| Lys | Glu | Phe | Glu | Lys | Leu | Asn | Arg | Ile | Gly | Glu | Gly | Thr | Tyr | Gly | Ile | |
| 10 | | | | | 15 | | | | | 20 | | | | | 25 | |

| GTG | TAT | CGG | GCC | CGG | GAC | ACC | CAG | ACA | GAT | GAG | ATT | GTC | GCA | CTG | AAG | 207 |
|---|---|---|---|---|---|---|---|---|---|---|---|---|---|---|---|---|
| Val | Tyr | Arg | Ala | Arg | Asp | Thr | Gln | Thr | Asp | Glu | Ile | Val | Ala | Leu | Lys | |
| | | | | 30 | | | | | 35 | | | | | 40 | | |

| AAG | GTG | CGG | ATG | GAC | AAG | GAG | AAG | GAT | GGC | ATC | CCC | ATC | AGC | AGC | TTG | 255 |
|---|---|---|---|---|---|---|---|---|---|---|---|---|---|---|---|---|
| Lys | Val | Arg | Met | Asp | Lys | Glu | Lys | Asp | Gly | Ile | Pro | Ile | Ser | Ser | Leu | |
| | | | 45 | | | | | 50 | | | | | 55 | | | |

| CGG | GAG | ATC | ACG | CTG | CTG | CTC | CGC | CTG | CGT | CAT | CCG | AAC | ATC | GTG | GAG | 303 |
|---|---|---|---|---|---|---|---|---|---|---|---|---|---|---|---|---|
| Arg | Glu | Ile | Thr | Leu | Leu | Leu | Arg | Leu | Arg | His | Pro | Asn | Ile | Val | Glu | |
| | | | 60 | | | | | 65 | | | | | 70 | | | |

| CTG | AAG | GAG | GTG | GTT | GTG | GGG | AAC | CAC | CTG | GAG | AGC | ATC | TTC | CTG | GTG | 351 |
|---|---|---|---|---|---|---|---|---|---|---|---|---|---|---|---|---|
| Leu | Lys | Glu | Val | Val | Val | Gly | Asn | His | Leu | Glu | Ser | Ile | Phe | Leu | Val | |
| | 75 | | | | | 80 | | | | | 85 | | | | | |

| ATG | GGT | TAC | TGT | GAG | CAG | GAC | CTG | GCC | AGC | CTC | CTG | GAG | AAT | ATG | CCA | 399 |
|---|---|---|---|---|---|---|---|---|---|---|---|---|---|---|---|---|
| Met | Gly | Tyr | Cys | Glu | Gln | Asp | Leu | Ala | Ser | Leu | Leu | Glu | Asn | Met | Pro | |
| 90 | | | | | 95 | | | | | 100 | | | | | 105 | |

| ACA | CCC | TTC | TCG | GAG | GCT | CAG | GTC | AAG | TGC | ATC | GTG | CTG | CAG | GTG | CTC | 447 |
|---|---|---|---|---|---|---|---|---|---|---|---|---|---|---|---|---|
| Thr | Pro | Phe | Ser | Glu | Ala | Gln | Val | Lys | Cys | Ile | Val | Leu | Gln | Val | Leu | |
| | | | | 110 | | | | | 115 | | | | | 120 | | |

| CGG | GGC | CTC | CAG | TAT | CTG | CAC | AGG | AAC | TTC | ATT | ATC | CAC | AGG | GAC | CTG | 495 |
|---|---|---|---|---|---|---|---|---|---|---|---|---|---|---|---|---|
| Arg | Gly | Leu | Gln | Tyr | Leu | His | Arg | Asn | Phe | Ile | Ile | His | Arg | Asp | Leu | |
| | | | 125 | | | | | 130 | | | | | 135 | | | |

| AAG | GTT | TCC | AAC | TTG | CTC | ATG | ACC | GAC | AAG | GGT | TGT | GTG | AAG | ACA | GCG | 543 |
|---|---|---|---|---|---|---|---|---|---|---|---|---|---|---|---|---|
| Lys | Val | Ser | Asn | Leu | Leu | Met | Thr | Asp | Lys | Gly | Cys | Val | Lys | Thr | Ala | |
| | | 140 | | | | | 145 | | | | | 150 | | | | |

| GAT | TTC | GGC | CTG | GCC | CGG | GCC | TAT | GGT | GTC | CCA | GTA | AAG | CCA | ATG | ACC | 591 |
|---|---|---|---|---|---|---|---|---|---|---|---|---|---|---|---|---|
| Asp | Phe | Gly | Leu | Ala | Arg | Ala | Tyr | Gly | Val | Pro | Val | Lys | Pro | Met | Thr | |
| | | 155 | | | | | 160 | | | | | 165 | | | | |

-continued

| | | | | | | | | | | | | | | | | |
|---|---|---|---|---|---|---|---|---|---|---|---|---|---|---|---|---|
| CCC | AAG | GTG | GTC | ACT | CTC | TGG | TAC | CGA | GCC | CCT | GAA | CTG | CTG | TTG | GGA | 639 |
| Pro 170 | Lys | Val | Val | Thr | Leu 175 | Trp | Tyr | Arg | Ala | Pro 180 | Glu | Leu | Leu | Leu | Gly 185 | |
| ACC | ACC | ACG | CAG | ACC | ACC | AGC | ATC | GAC | ATG | TGG | GCT | GTG | GGC | TGC | ATA | 687 |
| Thr | Thr | Thr | Gln | Thr 190 | Thr | Ser | Ile | Asp | Met 195 | Trp | Ala | Val | Gly | Cys 200 | Ile | |
| CTG | GCC | GAG | CTG | CTG | GCG | CAC | AGG | CCT | CTT | CTC | CCC | GGC | ACT | TCC | GAG | 735 |
| Leu | Ala | Glu | Leu 205 | Leu | Ala | His | Arg | Pro 210 | Leu | Leu | Pro | Gly | Thr 215 | Ser | Glu | |
| ATC | CAC | CAG | ATC | GAC | TTG | ATC | GTG | CAG | CTG | CTG | GGC | ACG | CCC | AGT | GAG | 783 |
| Ile | His | Gln 220 | Ile | Asp | Leu | Ile | Val 225 | Gln | Leu | Leu | Gly | Thr 230 | Pro | Ser | Glu | |
| AAC | ATC | TGG | CCG | GGC | TTT | TCC | AAG | CTG | CCA | CTG | GTC | GGC | CAG | TAC | AGC | 831 |
| Asn | Ile 235 | Trp | Pro | Gly | Phe | Ser 240 | Lys | Leu | Pro | Leu | Val 245 | Gly | Gln | Tyr | Ser | |
| CTC | CGG | AAG | CAG | CCC | TAC | AAC | AAC | CTG | AAG | CAC | AAG | TTC | CCA | TGG | CTG | 879 |
| Leu | Arg | Lys 250 | Gln | Pro | Tyr | Asn 255 | Asn | Leu | Lys | His | Lys 260 | Phe | Pro | Trp | Leu 265 | |
| TCG | GAG | GCC | GGG | CTG | CGC | CTG | CTG | CAC | TTC | CTG | TTC | ATG | TAC | GAC | CCT | 927 |
| Ser | Glu | Ala | Gly | Leu 270 | Arg | Leu | Leu | His | Phe 275 | Leu | Phe | Met | Tyr | Asp 280 | Pro | |
| AAG | AAA | AGG | GCG | ACG | GCC | GGG | GAC | TGC | CTG | GAG | AGC | TCC | TAT | TTC | AAG | 975 |
| Lys | Lys | Arg | Ala 285 | Thr | Ala | Gly | Asp | Cys 290 | Leu | Glu | Ser | Ser | Tyr 295 | Phe | Lys | |
| GAG | AAG | CCC | CTA | CGT | CTT | CCG | ATC | AGT | GGT | GTC | TGT | GAA | GGG | TGC | CGC | 1023 |
| Glu | Lys | Pro 300 | Leu | Arg | Leu | Pro | Ile 305 | Ser | Gly | Val | Cys | Glu 310 | Gly | Cys | Arg | |
| GAG | CCA | GGC | TGACCAGGCG | | CCCGGGATCC | | AGCTCATCCC | | CTTGGCTGGG | | | | | | | 1072 |
| Glu | Pro | Gly 315 | | | | | | | | | | | | | | |

| | |
|---|---|
| AACATCCTCC ACTGACTTCC TCCCACTGTC TGCCCTGAAC CCACTGCTGC CCCCAGAAAA | 1132 |
| AGGCCGGGTG ACACCGGGGG GCTCCCAGCC CGTGCACCCT GGAAGGGCAG GTCTGGCGGC | 1192 |
| TCCATCCGTG GCTGCAGGGG TCTCATGTGG TCCTCCTCGC TATGTTGGAA ATGTGCAACC | 1252 |
| ACTGCTTCTT GGGAGGAGTG GTGGGTGCAG TCCCCCGCT GTCTTTGAGT TGTGGTGGAC | 1312 |
| GCTGGCCTGG GATGAGAGGG CCCAGAAGAC CTTCGTATCC CCTCTCAGTC GCCCGGGGCT | 1372 |
| GTCCCGTGCA TGGGTTGGCT GTGGGGACCC CAGGTGGGCC TGGCAGGACT CC | 1424 |

( 2 ) INFORMATION FOR SEQ ID NO:4:

( i ) SEQUENCE CHARACTERISTICS:
        ( A ) LENGTH: 316 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Val 1 | Phe | Leu | Gly | Arg 5 | Cys | Arg | Ser | Val | Lys 10 | Glu | Phe | Glu | Lys | Leu Asn 15 |
| Arg | Ile | Gly | Glu 20 | Gly | Thr | Tyr | Gly | Ile 25 | Val | Tyr | Arg | Ala | Arg 30 | Asp Thr |
| Gln | Thr | Asp 35 | Glu | Ile | Val | Ala | Leu 40 | Lys | Lys | Val | Arg | Met 45 | Asp | Lys Glu |
| Lys | Asp 50 | Gly | Ile | Pro | Ile | Ser 55 | Ser | Leu | Arg | Glu | Ile 60 | Thr | Leu | Leu Leu |
| Arg 65 | Leu | Arg | His | Pro | Asn 70 | Ile | Val | Glu | Leu | Lys 75 | Glu | Val | Val | Val Gly 80 |

-continued

```
Asn His Leu Glu Ser Ile Phe Leu Val Met Gly Tyr Cys Glu Gln Asp
                85              90                    95
Leu Ala Ser Leu Leu Glu Asn Met Pro Thr Pro Phe Ser Glu Ala Gln
            100             105             110
Val Lys Cys Ile Val Leu Gln Val Leu Arg Gly Leu Gln Tyr Leu His
        115             120             125
Arg Asn Phe Ile Ile His Arg Asp Leu Lys Val Ser Asn Leu Leu Met
    130             135             140
Thr Asp Lys Gly Cys Val Lys Thr Ala Asp Phe Gly Leu Ala Arg Ala
145             150             155                             160
Tyr Gly Val Pro Val Lys Pro Met Thr Pro Lys Val Val Thr Leu Trp
                165             170             175
Tyr Arg Ala Pro Glu Leu Leu Leu Gly Thr Thr Thr Gln Thr Thr Ser
            180             185             190
Ile Asp Met Trp Ala Val Gly Cys Ile Leu Ala Glu Leu Leu Ala His
        195             200             205
Arg Pro Leu Leu Pro Gly Thr Ser Glu Ile His Gln Ile Asp Leu Ile
    210             215             220
Val Gln Leu Leu Gly Thr Pro Ser Glu Asn Ile Trp Pro Gly Phe Ser
225             230             235                             240
Lys Leu Pro Leu Val Gly Gln Tyr Ser Leu Arg Lys Gln Pro Tyr Asn
                245             250             255
Asn Leu Lys His Lys Phe Pro Trp Leu Ser Glu Ala Gly Leu Arg Leu
            260             265             270
Leu His Phe Leu Phe Met Tyr Asp Pro Lys Lys Arg Ala Thr Ala Gly
        275             280             285
Asp Cys Leu Glu Ser Ser Tyr Phe Lys Glu Lys Pro Leu Arg Leu Pro
    290             295             300
Ile Ser Gly Val Cys Glu Gly Cys Arg Glu Pro Gly
305             310             315
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:5:

```
Lys Leu Ala Asp Phe Gly Leu Ala Arg
1               5
```

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:6:

```
Lys Thr Ala Asp Phe Gly Leu Ala Arg
1               5
```

(2) INFORMATION FOR SEQ ID NO:7:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:7:

```
Pro  Ile  Thr  Ala  Leu  Arg  Glu
1                   5
```

( 2 ) INFORMATION FOR SEQ ID NO:8:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:8:

```
GCAGGATCCC GARAARAT Y G GNGARGGNAC NTA                                    33
```

( 2 ) INFORMATION FOR SEQ ID NO:9:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:9:

```
Glu  Lys  Ile  Gly  Glu  Gly  Thr  Tyr
1                   5
```

( 2 ) INFORMATION FOR SEQ ID NO:10:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:10:

```
CGGCTGCAGA RNA Y Y TCNGG NGMNCKRTAC CA                                    32
```

( 2 ) INFORMATION FOR SEQ ID NO:11:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:11:

```
Trp  Tyr  Arg  Ser  Pro  Glu  Val  Leu
1                   5
```

( 2 ) INFORMATION FOR SEQ ID NO:12:

( i ) SEQUENCE CHARACTERISTICS:
      ( A ) LENGTH: 7 amino acids ( B ) TYPE: amino acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:12:

Pro  Ser  Thr  Ala  Ile  Arg  Glu
    1                   5

( 2 ) INFORMATION FOR SEQ ID NO:13:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:13:

Glu  Lys  Ile  Gly  Glu  Gly  Thr  Tyr
    1                   5

( 2 ) INFORMATION FOR SEQ ID NO:14:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:14:

Trp  Tyr  Arg  Ser  Pro  Glu  Val  Leu
    1                   5

( 2 ) INFORMATION FOR SEQ ID NO:15:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:15:

GTGCAGATAC TGGAGGCCCC GGAG                                              24

( 2 ) INFORMATION FOR SEQ ID NO:16:

( i ) SEQUENCE CHARACTERISTICS:
            ( A ) LENGTH: 33 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:16:

CTCCTCGAGT GACCTGAGCC TCCGAGAAGG GTG                                    33

( 2 ) INFORMATION FOR SEQ ID NO:17:

( i ) SEQUENCE CHARACTERISTICS:
            ( A ) LENGTH: 36 base pairs
            ( B ) TYPE: nucleic acid
            ( C ) STRANDEDNESS: single (D) TOPOLOGY: linear (ii) MOLECULE TYPE: cDNA (xi) SEQUENCE DESCRIPTION: SEQ ID NO:17:

CTCGGATCCG GAATTCCCGT ATTCCTGGGA CGATGC    36

(2) INFORMATION FOR SEQ ID NO:18:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:18:

CTCGGATCCG GAATTCCCGT GAAGGAGTTT GAGAAG    36

(2) INFORMATION FOR SEQ ID NO:19:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:19:

CAGGAATTCC GGAGTCCTGC CAGGC    25

(2) INFORMATION FOR SEQ ID NO:20:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:20:

ACCTCGGAGC TGAATACA    18

(2) INFORMATION FOR SEQ ID NO:21:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:21:

TTCCTTGGAG AAGCAGAG    18

(2) INFORMATION FOR SEQ ID NO:22:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:22:

GTGGACCACG AAGAGTTA                                                                        18

( 2 ) INFORMATION FOR SEQ ID NO:23:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:23:

CTCTTGCCAC TCGTACTT                                                                        18

( 2 ) INFORMATION FOR SEQ ID NO:24:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:24:

ACATCCTCCA CTGACTTC                                                                        18

( 2 ) INFORMATION FOR SEQ ID NO:25:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:25:

TCCCAAGAAG CAGTGGTT                                                                        18

( 2 ) INFORMATION FOR SEQ ID NO:26:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:26:

TTGCCACTAG GGCTCTTG                                                                        18

( 2 ) INFORMATION FOR SEQ ID NO:27:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:27:

CAGCAAGGAC AAGACA                                                                          16

( 2 ) INFORMATION FOR SEQ ID NO:28:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:28:

```
TGATCCTGCG GAGAACACCC TTGG                                    24
```

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

```
ACTGCAGAGA CATGGAAGAG GCGA                                    24
```

( 2 ) INFORMATION FOR SEQ ID NO:30:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Met Ala Lys Gln Tyr Asp Ser Val Glu Cys Pro Phe Cys Asp Glu Val
 1               5                  10                  15

Ser Lys Tyr Glu Lys Leu Ala Lys Ile Gly Gln Gly Thr Phe Gly Glu
                20                  25                  30

Val Phe Lys Ala Arg His Arg Lys Thr Gly Gln Lys Val Ala Leu Lys
            35                  40                  45

Lys Val Leu Met Glu Asn Glu Lys Glu Gly Phe Pro Ile Thr Ala Leu
    50                  55                  60

Arg Glu Ile Lys Ile Leu Gln Leu Leu Lys His Glu Asn Val Val Asn
65                  70                  75                  80

Leu Ile Glu Ile Cys Arg Thr Lys Ala Ser Pro Tyr Asn Arg Cys Lys
                85                  90                  95

Gly Ser Ile Tyr Leu Val Phe Asp Phe Cys Glu His Asp Leu Ala Gly
            100                 105                 110

Leu Leu Ser Asn Val Leu Val Lys Phe Thr Leu Ser Glu Ile Lys Arg
        115                 120                 125

Val Met Gln Met Leu Leu Asn Gly Leu Tyr Tyr Ile His Arg Asn Lys
    130                 135                 140

Ile Leu His Arg Asp Met Lys Ala Ala Asn Val Leu Ile Thr Arg Asp
145                 150                 155                 160

Gly Val Leu Lys Leu Ala Asn Phe Gly Leu Ala Arg Ala Phe Ser Leu
                165                 170                 175

Ala Lys Asn Ser Gln Pro Asn Arg Tyr Thr Asn Arg Val Val Thr Leu
            180                 185                 190

Trp Tyr Arg Pro Pro Glu Leu Leu Leu Gly Glu Arg Asp Tyr Gly Pro
        195                 200                 205

Pro Ile Asp Leu Trp Gly Ala Gly Cys Ile Met Ala Glu Met Trp Thr
```

```
                  210                    215                    220

Arg  Ser  Pro  Ile  Met  Gln  Gly  Asn  Thr  Glu  Gln  His  Gln  Leu  Ala  Leu
225                      230                      235                      240

Ile  Ser  Gln  Leu  Cys  Gly  Ser  Ile  Thr  Pro  Glu  Val  Trp  Pro  Asn  Val
                    245                      250                      255

Asp  Asn  Tyr  Glu  Leu  Tyr  Glu  Lys  Leu  Glu  Leu  Val  Lys  Gly  Gln  Lys
               260                      265                      270

Arg  Lys  Val  Lys  Asp  Arg  Leu  Lys  Ala  Tyr  Val  Arg  Asp  Pro  Tyr  Ala
          275                      280                      285

Leu  Asp  Leu  Ile  Asp  Lys  Leu  Leu  Val  Leu  Asp  Pro  Ala  Gln  Arg  Ile
     290                      295                      300

Asp  Ser  Asp  Asp  Ala  Leu  Asn  His  Asp  Phe  Phe  Trp  Ser  Asp  Pro  Met
305                      310                      315                      320

Pro  Ser  Asp  Leu  Lys  Gly  Met  Leu  Ser  Thr  His  Leu  Thr  Ser  Met  Phe
                    325                      330                      335

Glu  Tyr  Leu  Ala  Pro  Pro  Arg  Arg  Lys  Gly  Ser  Gln  Ile  Thr  Gln  Gln
               340                      345                      350

Ser  Thr  Asn  Gln  Ser  Arg  Asn  Pro  Ala  Thr  Thr  Asn  Gln  Thr  Glu  Phe
          355                      360                      365

Glu  Arg  Val  Phe
370
```

( 2 ) INFORMATION FOR SEQ ID NO:31:

( i ) SEQUENCE CHARACTERISTICS:
        ( A ) LENGTH: 316 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
Val  Phe  Leu  Gly  Arg  Cys  Arg  Ser  Val  Lys  Glu  Phe  Glu  Lys  Leu  Asn
 1                  5                       10                       15

Arg  Ile  Gly  Glu  Gly  Thr  Tyr  Gly  Ile  Val  Tyr  Arg  Ala  Arg  Asp  Thr
               20                       25                       30

Gln  Thr  Asp  Glu  Ile  Val  Ala  Leu  Lys  Lys  Val  Arg  Met  Asp  Lys  Glu
          35                       40                       45

Lys  Asp  Gly  Ile  Pro  Ile  Ser  Ser  Leu  Arg  Glu  Ile  Thr  Leu  Leu  Leu
     50                       55                       60

Arg  Leu  Arg  His  Pro  Asn  Ile  Val  Glu  Leu  Lys  Glu  Val  Val  Val  Gly
65                       70                       75                       80

Asn  His  Leu  Glu  Ser  Ile  Phe  Leu  Val  Met  Gly  Tyr  Cys  Glu  Gln  Asp
                    85                       90                       95

Leu  Ala  Ser  Leu  Leu  Glu  Asn  Met  Pro  Thr  Pro  Phe  Ser  Glu  Ala  Gln
               100                      105                      110

Val  Lys  Cys  Ile  Val  Leu  Gln  Val  Leu  Arg  Gly  Leu  Gln  Tyr  Leu  His
          115                      120                      125

Arg  Asn  Phe  Ile  Ile  His  Arg  Asp  Leu  Lys  Val  Ser  Asn  Leu  Leu  Met
     130                      135                      140

Thr  Asp  Lys  Gly  Cys  Val  Lys  Thr  Ala  Asn  Phe  Gly  Leu  Ala  Arg  Ala
145                      150                      155                      160

Tyr  Gly  Val  Pro  Val  Lys  Pro  Met  Thr  Pro  Lys  Val  Val  Thr  Leu  Trp
                    165                      170                      175

Tyr  Arg  Ala  Pro  Glu  Leu  Leu  Leu  Gly  Thr  Thr  Gln  Thr  Thr  Ser
               180                      185                      190
```

-continued

| Ile | Asp | Met 195 | Trp | Ala | Val | Gly | Cys 200 | Ile | Leu | Ala | Glu | Leu 205 | Leu | Ala | His |
| --- | --- | --- | --- | --- | --- | --- | --- | --- | --- | --- | --- | --- | --- | --- | --- |
| Arg | Pro 210 | Leu | Leu | Pro | Gly | Thr 215 | Ser | Glu | Ile | His | Gln 220 | Ile | Asp | Leu | Ile |
| Val 225 | Gln | Leu | Leu | Gly | Thr 230 | Pro | Ser | Glu | Asn | Ile 235 | Trp | Pro | Gly | Phe | Ser 240 |
| Lys | Leu | Pro | Leu | Val 245 | Gly | Gln | Tyr | Ser | Leu 250 | Arg | Lys | Gln | Pro | Tyr 255 | Asn |
| Asn | Leu | Lys | His 260 | Lys | Phe | Pro | Trp | Leu 265 | Ser | Glu | Ala | Gly | Leu 270 | Arg | Leu |
| Leu | His | Phe 275 | Leu | Phe | Met | Tyr | Asp 280 | Pro | Lys | Lys | Arg | Ala 285 | Thr | Ala | Gly |
| Asp | Cys 290 | Leu | Glu | Ser | Ser | Tyr 295 | Phe | Lys | Glu | Lys | Pro 300 | Leu | Arg | Leu | Pro |
| Ile 305 | Ser | Gly | Val | Cys | Glu 310 | Gly | Cys | Arg | Glu | Pro 315 | Gly | | | | |

HUMAN CYCLIN-DEPENDENT KINASE-LIKE PROTEINS AND METHODS OF USING THE SAME

ACKNOWLEDGEMENT OF GOVERNMENT RIGHTS

This invention was made with Government support from the National Cancer Institute under Grant Number R1-C860999-01. The Government has certain rights in this invention.

FIELD OF THE INVENTION

The invention relates to the identification and cloning of human cdc2-related kinases, to methods of making and using the same, and to compositions and methods of inhibiting their activity in the cell cycle.

BACKGROUND OF THE INVENTION

Cell division, cell growth and cell differentiation are complex processes which are regulated to a great extent by phosphorylation/dephosphorylation events. Thus, protein kinases and phosphatases play a major role in cell regulation. The members of the protein kinase family are known to modulate the activity of a wide variety of proteins, including kinases, phosphatases, transcription factors, cyclins, metabolic enzymes and structural proteins, among others. The cell cycle is regulated, at least in part, by a subfamily of protein kinases called cyclin-dependent kinases (CDKS). These protein kinases contain a catalytic domain that requires the association of a regulatory subunit called cyclin, which is necessary for the kinase activity of the complex. Cyclin/CDK complexes have been shown to be required at different points of the cell cycle. In vertebrates, CDK2 is required for DNA synthesis probably associated to cyclin E. The transition from interphase to mitosis requires the activity of CDC2, which is associated to cyclin B. Moreover, CDK4/ and CDK6/D-type cyclin complexes appear to link growth factor stimulation to cell cycle progression. The role of CDK5 in the cell cycle is controversial. Although this kinase associates with D-type cyclins, it is expressed at high levels in terminally differentiated neuronal cells and appears to be involved in the phosphorylation of neurofilaments.

Orderly progression through the cell cycle in yeast requires the association of a single cyclin-dependent kinase (cdk), p34/cdc2/CDC28, with cyclins to form active phosphorylating complexes which regulate both the G1/S and G2/M transitions. With the discovery and characterization of several murine and human cdc2-related kinases, it has become apparent that mammalian cell cycle systems operate under a much higher degree of complexity. Several different cyclin-cdk complexes have been found active at different stages in the cell cycle.

Components of the cell cycle regulatory machinery have been found to be involved in several human cancers. Cyclin dependent kinases, their regulatory subunits or cyclins, cyclin-dependent kinase inhibitors, as well as the associated tumor suppressor proteins p53 and pRb, have been found to be deregulated or mutated in numerous human tumors. The transforming activity of DNA tumor virus proteins E1A, SV40 large T, and E7 is exerted, at least in part, through their binding of the growth suppressor pRb and consequent release of E2F. In addition, E1A has been shown to bind to cyclin A/cdk2 complexes, providing the first direct link between the cell cycle and a transformed phenotype.

Cell proliferation disorder is implicated in certain diseases such as psoriasis, vascular disease and cancer. There is a need to identify compounds which inhibit the undesirable cell proliferation associated with cancer. Specifically, safe and effective compounds are sought which reduce the abnormal cell proliferation which is characteristic of cancer by interfering with the molecular signals that participate in the unrestrained reproduction and multiplication of malignant cells. Specifically, safe and effective compounds are sought which interfering with the molecular signals that participate in the unrestrained reproduction and multiplication of cells whose abnormal cell proliferation characteristic of diseases, disorders and conditions such as cancer, psoriasis and vascular diseases and disorders.

SUMMARY OF THE INVENTION

The present invention relates to substantially pure human cyclin-dependent kinase-like proteins PITALRE and PISSLRE.

The present invention relates to isolated protein complex that comprise PITALRE or PISSLRE.

The present invention relates isolated nucleic acid molecule that encode PITALRE or PISSLRE, or a fragment thereof.

The present invention relates to recombinant expression vectors that comprise nucleic acid sequences that encode PITALRE or PISSLRE.

The present invention relates to host cells that comprise recombinant expression vectors which include nucleic acid sequences that encode PITALRE or PISSLRE.

The present invention relates to oligonucleotide molecules that consist of a nucleotide sequence complimentary to a portion of the nucleotide sequence that encodes PITALRE or PISSLRE.

The present invention relates to isolated antibody which binds to an epitope on PITALRE or PISSLRE.

The present invention relate to isolated nucleic acid molecules that comprises a nucleotide sequence that encodes phosphorylation deficient PITALRE or a phosphorylation deficient PISSLRE.

The present invention relate to recombinant vectors that comprise a nucleotide sequence that encodes phosphorylation deficient PITALRE or a phosphorylation deficient PISSLRE.

The present invention relates to pharmaceutical compositions comprising a pharmaceutically acceptable carrier and nucleic acid molecules that comprise nucleotide sequences that encode phosphorylation deficient PITALRE or a phosphorylation deficient PISSLRE.

The present invention relates to methods, kits and reagents useful to identify compounds that inhibit the phosphorylation activity of PITALRE.

Figure 1:
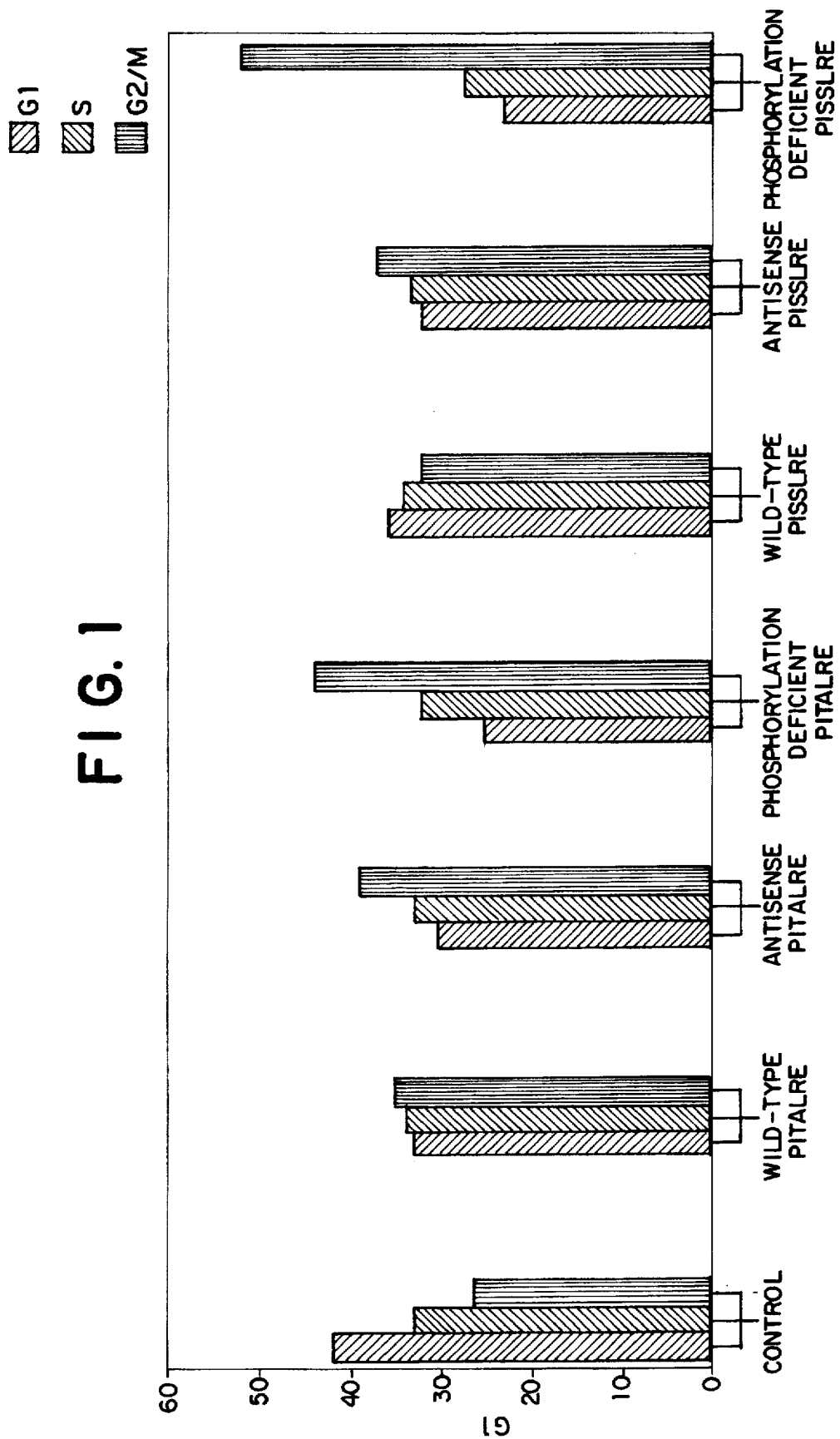
FIG. 1 shows data from experiments which compare the percentage of cells at each of three stages of the cell cycle ($G_1$, S and $G_2$/M) when gene constructs encoding one of wild-type PITALRE, antisense PITALRE, phosphorylation deficient PITALRE, wild-type PISSLRE, antisense PISSLRE, phosphorylation deficient PISSLRE, and control are introduced. DETAILED DESCRIPTION OF THE INVENTION Two new cdc2-related kinases, PISSLRE and PITALRE, have been discovered. These proteins have been found to be involved in the progress of a cell through the cell cycle, specifically the $G_2$/M transition which results in cell division into two cells at $G_1$. It has been discovered that the presence of non-functional PISSLRE or PITALRE blocks the cell from completing the $G_2$ transition. The inhibition of either PISSLRE or PITALRE activity will thus inhibit cell division.

A number of diseases are characterized by a loss of control of the cell cycle and a resultant uncontrolled cell division. Uncontrolled cell proliferation is a primary characteristic of all forms of cancer as well as psoriasis, hyperplasia and other diseases and disorders characterized by cell proliferation. The ability to block cell division by inhibiting the activity of either PISSLRE or PITALRE thereby provides a means to treat individuals suffering from diseases and disorders characterized by uncontrolled cell proliferation. The discovery of PISSLRE and PITALRE, and that each, respectively, plays a role in the cell cycle provides drug targets against which inhibitors can be identified and/or designed. Such inhibitors are useful to block cell division, which is a particular strategy foranti-cancer drugs.

PISSLRE and PITALRE have been purified; complexes which include the proteins have been isolated; hybridomas which produce antibodies that bind to the proteins have been generated; cDNAs that encodes these proteins have been isolated, sequenced, incorporated into vectors including expression vector which were introduced into host cells that then express the proteins recombinantly. Phosphorylation deficient mutants of PISSLRE and PITALRE have been designed block $G_2$ transition. Nucleic acids encoding these mutants have been produced as have antisense molecules against PISSLRE and PITALRE.

The discovery of PISSLRE and PITALRE provides the means to design and discovery of specific inhibitors. According to the present invention, these proteins may be used to screen compounds for specific inhibitors. Inhibitors are useful as anti-cancer agents. Purified PISSLRE or PITALRE, and complexes which include PISSLRE or PITALRE may be used in drug screens to determine whether or not these proteins and complexes are active in the presence of test compounds. Test compounds may be screened to identify compounds which dissociate the complexes and inhibit the formation of complexes.

Hybridomas which produce antibodies that bind to PISSLRE or PITALRE, and the antibodies themselves, are useful in the isolation and purification of PISSLRE or PITALRE and protein complexes that include PISSLRE or PITALRE. In addition, antibodies are specific inhibitors of PITALRE or PISSLRE activity.

Isolated cDNA that encodes these proteins is useful as a starting material in the production of mutants as well as the recombinant production of the proteins. The cDNA is incorporated into vectors including expression vectors which are introduced into host cells that then express the proteins recombinantly. Nucleic acid molecules and fragments thereof, particularly genomic sequences may be used as probes to detect genetic rearrangements. Probes are useful, for example, in restriction fragment length polymorphism assays and fluorescence in situ hybridization assays. Nucleic acid molecules which comprise a nucleotide sequence which are complementary to fragments of the cDNA that encodes PISSLRE or PITALRE may be used as antisense molecules and primers to inhibit translation of mRNA and amplify genetic sequences, respectively.

Nucleic acids encoding phosphorylation deficient mutants of PISSLRE and PITALRE may be delivered to cells to block cell divisions. Such nucleic acid molecules may be included within delivery vehicles and/or formulated with pharmaceutically acceptable carriers for administration into animals as a pharmaceutical.

PITALRE is encoded by cDNA shown in SEQ ID NO:1 and has an amino acid sequence shown in SEQ ID NO:2. PITALRE is a nuclear localized kinase that, although not able to act on histone H1, is able to phosphorylate pRb on serine residues in vitro. This would indicate a function not unlike cdk4 or cdk6; however, this kinase activity has not been found to be cell cycle regulated.

PISSLRE is encoded by cDNA shown in SEQ ID NO:3 and has an amino acid sequence shown in SEQ ID NO:4. PISSLRE, shares 47% identity with cdc2 and contains many conserved motifs of cdks including the proline in its PSTAIRE-like sequence and target residues for cdk activating kinase (CAK) phosphorylation. Both of these motifs are needed for cyclin binding and stabilization. The PISSLRE gene is predominantly expressed in terminally differentiated tissues, possibly indicating a functional relation to cdk5, which is specifically expressed in nonproliferating neural tissue.

PITALRE and PISSLRE can be isolated from natural sources, produced by recombinant DNA methods or synthesized by standard protein synthesis techniques.

Antibodies which specifically bind to PITALRE or PISSLRE may be used to purify the protein from natural sources using well known techniques and readily available starting materials. Such antibodies may also be used to purify the protein from material present when producing the protein by recombinant DNA methodology.

As used herein, the term "antibody" is meant to refer to complete, intact antibodies, and Fab fragments and $F(ab)_2$ fragments thereof. Complete, intact antibodies include monoclonal antibodies such as murine monoclonal antibodies, chimeric antibodies and humanized antibodies. In some embodiments, the antibodies specifically bind to an epitope of SEQ ID NO:2 or SEQ ID NO:4 but not both. Antibodies that bind to an epitope which is present one of these proteins is useful to isolate and purify that protein from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and $F(ab)_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, PITALRE or PISSLRE, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the PITALRE or PISSLRE (depending upon which was injected into the mouse), the hybridoma which produces them is cultured to produce a continuous supply of antibodies.

Using standard techniques and readily available starting materials, a nucleic acid molecule that encodes PITALRE or PISSLRE may be isolated from a cDNA library, using probes which are designed using the nucleotide sequence information disclosed in SEQ ID NO:1 or SEQ ID NO:3. The present invention relates to an isolated nucleic acid molecule that comprises a nucleotide sequence that encodes PITALRE or PISSLRE. The present invention relates to an isolated nucleic acid molecule that comprises a nucleotide sequence that encodes the amino acid sequence of SEQ ID NO:2 or SEQ ID NO:4. In some embodiments, the nucleic acid molecules consist of a nucleotide sequence that encodes PITALRE or PISSLRE. In some embodiments, the nucleic acid molecules comprise the nucleotide sequence that consists of the coding sequence in SEQ ID NO:1 or SEQ ID NO:3. In some embodiments, the nucleic acid molecules consist of the nucleotide sequence set forth in SEQ ID NO:1 or SEQ ID NO:3. The isolated nucleic acid molecules of the invention are useful to prepare constructs and recombinant expression systems for preparing proteins of the invention.

A cDNA library may be generated by well known techniques. A cDNA clone which contains one of the nucleotide sequences described herein may be identified using probes that comprise at least a portion of the nucleotide sequence disclosed in SEQ ID NO:1 or SEQ ID NO:3. The probes have at least 16 nucleotides, preferably at least 24 nucleotides. The probes are used to screen the cDNA library using standard hybridization techniques. Alternatively, genomic clones may be isolated using genomic DNA from any human cell as a starting material.

The present invention relates to isolated nucleic acid molecules that comprise a nucleotide sequence identical or complementary to a fragment of SEQ ID NO:1 or SEQ ID NO:3 which is at least 10 nucleotides. In some embodiments, the isolated nucleic acid molecules consist of a nucleotide sequence identical or complementary to a fragment of SEQ ID NO:1 or SEQ ID NO:3 which is at least 10 nucleotides. In some embodiments, the isolated nucleic acid molecules comprise or consist of a nucleotide sequence identical or complementary to a fragment of SEQ ID NO:1 or SEQ ID NO:3 which is 15–150 nucleotides. In some embodiments, the isolated nucleic acid molecules comprise or consist of a nucleotide sequence identical or complementary to a fragment of SEQ ID NO:1 or SEQ ID NO:3 which is 15–30 nucleotides. Isolated nucleic acid molecules that comprise or consist of a nucleotide sequence identical or complementary to a fragment of SEQ ID NO:1 or SEQ ID NO:3 which is at least 10 nucleotides are useful as probes for identifying genes and cDNA sequence having SEQ ID NO:1 or SEQ ID NO:3, respectively, PCR primers for amplifying genes and cDNA having SEQ ID NO:1 or SEQ ID NO:3, respectively, and antisense molecules for inhibiting transcription and translation of genes and cDNA, respectively, which encode PITALRE or PISSLRE having the amino acid sequence of SEQ ID NO:2 or SEQ ID NO:4, respectively.

The cDNA that encodes PITALRE or PISSLRE may be used as a molecular marker in electrophoresis assays in which cDNA from a sample is separated on an electrophoresis gel and PITALRE or PISSLRE probes are used to identify bands which hybridize to such probes. Specifically, SEQ ID NO:1 or portions thereof and SEQ ID NO:3 or portions thereof, may be used as a molecular marker in electrophoresis assays in which cDNA from a sample is separated on an electrophoresis gel and PITALRE or PISSLRE specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes PITALRE and PISSLRE, respectively. Electrophoresis gels useful in such an assay include standard polyacrylamide gels as described in Sambrook et al., *Molecular Cloning a Laboratory Manual*, Second Ed. Cold Spring Harbor Press (1989) which is incorporated herein by reference.

The nucleotide sequences in SEQ ID NO:1 and SEQ ID NO:3 may be used to design probes, primers and complimentary molecules which specifically hybridize to the unique nucleotide sequences of PITALRE and PISSLRE, respectively. Probes, primers and complimentary molecules which specifically hybridize to nucleotide sequence that encodes PITALRE or PISSLRE may be designed routinely by those having ordinary skill in the art.

The present invention also includes labelled oligonucleotides which are useful as probes for performing oligonucleotide hybridization methods to identify PITALRE or PISSLRE. Accordingly, the present invention includes probes that can be labelled and hybridized to unique nucleotide sequences of PITALRE or PISSLRE. The labelled probes of the present invention are labelled with radiolabelled nucleotides or are otherwise detectable by readily available non-radioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of PITALRE or PISSLRE.

In some embodiments, labelled probes are used to determine on which chromosome the PITALRE or PISSLRE genes are present. Such labelled probes comprise some or all of SEQ ID NO:1 or SEQ ID NO:3. As discussed in Example 3, PITALRE has been mapped to chromosome 9 and PISSLRE has been mapped on chromosome 16. Using the probes of the invention, translocations of chromosome 9 which include the PITALRE gene or translocation of chromosome 16 which include the PISSLRE gene can be detected. In a one preferred embodiments, fluorescent labelled PITALRE probes which are labelled with one fluorescent color are used in conjunction with a fluorescent labelled probe for the chromosome 9 centromere that is labelled with another color. The proximity of the two different colored probes hybridized to the genetic material in a single cell is useful to detect chromosome 9 translocations. In another preferred embodiment, fluorescent labelled PISSLRE probes which are labelled with one fluorescent color are used in conjunction with a fluorescent labelled probe for the chromosome 16 centromere that is labelled with another color. The proximity of the two different colored probes hybridized to the genetic material in a single cell is useful to detect chromosome 16 translocations.

The cDNA that encodes PITALRE or PISSLRE may be used to design PCR primers for amplifying nucleic acid sequences. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

The present invention relates to a recombinant expression vector that comprises a nucleotide sequence that encodes PITALRE or PISSLEE that comprises the amino acid sequence of SEQ ID NO:2 or SEQ ID NO:4, respectively. As used herein, the term "recombinant expression vector" is meant to refer to a plasmid, phage, viral particle or other vector which, when introduced into an appropriate host, contains the necessary genetic elements to direct expression of the coding sequence that encodes PITALRE or PISSLRE. One having ordinary skill in the art can isolate the nucleic acid molecule that encodes PITALRE or PISSLRE and insert it into an expression vector using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:1 or SEQ ID NO:3. The recombinant expression vectors of the invention are useful for transforming hosts which the express PITALRE or PISSLEE.

The present invention relates to a host cell that comprises the recombinant expression vector that includes a nucleotide sequence that encodes PITALRE or PISSLRE that comprises SEQ ID NO:1 or SEQ ID NO:3. In some embodiments, the host cell comprises a recombinant expression vector that comprises SEQ ID NO:1 or SEQ ID NO:3. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes the PITALRE or PISSLRE that comprises the amino acid sequence of SEQ ID NO:2 or SEQ ID NO:4. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes PITALRE or PISSLRE is operably linked to a mammary cell specific promoter whereby the coding sequence is only expressed in mammary cells and the recombinant protein so expressed is recovered from the animal's milk. In some embodiments, the coding sequence that encodes PITALRE or PISSLRE is SEQ ID NO:1 or SEQ ID NO:3.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of PITALRE or PISSLRE in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (invitrogen, San Diego, Calif.) may, for example, be used for production in mammalian cells such as Chinese Hamster Ovary cells. One having ordinary skill in the art can use these commercial expression vectors and systems or others to produce PITALRE or PISSLRE routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

The expression vector including the DNA that encodes PITALRE or PISSLRE is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate PITALRE or PISSLRE that is produced using such expression systems. The methods of purifying PITALRE or PISSLRE from natural sources using antibodies which specifically bind to PITALRE or PISSLRE as described above, may be equally applied to purifying PITALRE or PISSLRE produced by recombinant DNA methodology.

Examples of genetic constructs include the PITALRE or PISSLRE coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes PITALRE or PISSLRE from readily available starting materials. Such gene constructs are useful for the production of PITALRE or PISSLRE.

In some embodiments of the invention, transgenic non-human animals are generated. The transgenic animals according to the invention contain SEQ ID NO:1 or SEQ ID NO:3 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce PITALRE or PISSLRE. Preferred animals are rodents, particularly goats, rats and mice.

In addition to producing these proteins by recombinant techniques, automated peptide synthesizers may also be employed to produce PITALRE or PISSLRE. Such techniques are well known to those having ordinary skill in the art and are useful if derivatives which have substitutions not provided for in DNA-encoded protein production.

According to another aspect of the invention, nucleic acid molecules that encode phosphorylation deficient PITALRE or PISSLRE can be used in gene therapy to inhibit PITALRE or PISSLRE activity and thereby inhibit cell division associated with diseases such as cancer. By introducing into cells the cDNA that encodes either PITALRE or PISSLRE in an expressible form, PITALRE or PISSLRE will be expressed and inhibit PITALRE or PISSLRE activity.

The region responsible for phosphorylation activity in cdc2 related kinases is KLADFGLAR (SEQ ID NO:5). In PITALRE, that sequence is present. In PISSLRE, the sequence is KTADFGLAR (SEQ ID NO:6). One way to generate phosphorylation deficient mutants of PITALRE or PISSLRE is to substitute an asparagine in place of the aspartic acid in this sequence. In addition, other substitutions, insertions and/or deletions in the consensus sequence or truncated forms of PITALRE and PISSLRE in which all or part of the consensus sequence are deleted. In preferred embodiments, the portion of PITALRE or PISSLRE which is present in the phosphorylation deficient PITALRE or PISSLRE includes the portion which participates in complex formation with other proteins.

Nucleic acid molecules that encode phosphorylation deficient PITALRE or PISSLRE may be delivered using any one of a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, transferrin-mediated transfection and other receptor-mediated means. The invention is intended to include such other forms of expression vectors and other suitable delivery means which serve equivalent functions and which become known in the art subsequently hereto.

In a preferred embodiment of the present invention, DNA is delivered to competent host cells by means of an adenovirus. One skilled in the art would readily understand this technique of delivering DNA to a host cell by such means. Although the invention preferably includes adenovirus, the invention is intended to include any virus which serves equivalent functions.

In another preferred embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another preferred embodiment of the present invention, nucleic acid is delivered through folate receptor means. The nucleic acid sequence to be delivered to a host cell is linked to polylysine and the complex is delivered to the tumor cell by means of the folate receptor. U.S. Pat. No. 5,108,921 issued Apr. 28, 1992 to Low et al., which is incorporated herein by reference, describes such delivery components.

Pharmaceutical compositions according to the invention include delivery components in combination with nucleic acid molecules which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention.

Another aspect of the present invention is a method of treating an individual suspected of undergoing cellular transformation by administering to the individual a pharmaceutical composition comprising a nucleic acid sequence in combination with delivery components, in an amount sufficient to reverse the transformation. The nucleic acid sequence encodes a protein that lacks phosphorylation activity. Individuals suffering from tumors may be identified using well known techniques. Biopsies may be routinely performed.

Pharmaceutical compositions may be formulated by one having ordinary skill in the art with compositions selected depending upon the chosen mode of administration. Suitable pharmaceutical carriers are described in *Remington's Pharmaceutical Sciences*, A. Osol, a standard reference text in this field, which is incorporated herein by reference.

The pharmaceutical compositions of the present invention may be administered by any means that enables the active agent to reach the agent's site of action in the body of a mammal. Pharmaceutical compositions may be administered parenterally, i.e., intravenous, subcutaneous, intramuscular. Intravenous administration is the preferred route.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

According to the invention, compounds may be identified which inhibit PITALRE-mediated phosphorylation of $p56^{RB}$. In some embodiments, in vitro assays are provided which compare the phosphorylation activity of PITALRE immunocomplexes in the presence or absence of test compounds.

In preferred embodiments, bacterially produced $p56^{RB}$ is used as a substrate. The immunocomplexes also phosphorylate myelin basic protein (MBP) and casein, but at a lower level than when the $p56^{RB}$. Thus, MBP or casein may also be used as a substrate.

PITALRE immunocomplexes are obtained from HeLa cells. After serum deprivation and blocking with hydroxyurea, HeLa cells were allowed to progress through the cell cycle in a synchronous fashion. Cell fractions were lysed, and the protein extracts were immunoprecipitated with affinity purified anti-PITALRE.

In vitro kinase assays are performed using [gamma$^{32}$P] ATP.

A test assay is performed by combining PITALRE immunocomplexes, [gamma$^{32}$P]ATP and substrate in the presence of a test compound under conditions in which the substrate would undergo PITALRE immunocomplex mediated phosphorylated with the $^{32}$P in the absence of the test compound. The level of substrate phosphorylation that occurs is measured and compared to the level that occurs in control assays, i.e. conditions in which the substrate would undergo PITALRE immunocomplex mediated phosphorylated with the $^{32}$P in the absence of the test compound. Phosphorylation levels are measured by standard techniques well known and readily available to those having skill in the art. If the level of phosphorylation in the test assay is lower than that in the control assay, the test compound is a PITALRE-inhibitor candidate.

The method of the present invention comprises the steps of contacting PITALRE immunocomplexes and bacterially produced p56$^{RB}$, MBP or casein in the presence of [gamma$^{32}$P]ATP and a test compound under conditions in which PITALRE would phosphorylate p56$^{RB}$, MBP or casein using the $^{32}$P of the ATP in the absence of the test compound. Thus, if the test compound inhibits the phosphorylation activity of PITALRE, the substrate with not be phosphorylated. Since the ATP is radiolabelled, phosphorylation can be detected using standard techniques. The level of phosphorylation that takes place in the presence of the test compound is compared to the level that occurs in a control assay performed without the test compound.

The PITALRE immunocomplex used in the kinase assay is generally that which is present in about 200 μg of total protein from cell lysates. Anti-PITALRE antibodies are used to isolate the PITALRE immunocomplex from the total protein of cell lysates. Preferred cells include HeLa cells and ML-1 cells.

A preferred range of the amount of p56$^{RB}$ is 0.1–10 μg. A preferred amount of p56$^{RB}$ is 0.25–1.0 μg.

A preferred range of the amount of MBP is 0.1–10 μg. A preferred amount of MBP is 2.5 μg.

A preferred range of the amount of casein is 0.1–10 μg.

[gamma$^{32}$P]ATP is preferably about 3000 Ci/mmol, 10 mCi/ml, 6.66×10$^6$ cpm/pmol. A preferred volume of [gamma$^{32}$P]ATP is about 30–50:1 total reaction:ATP.

In some embodiments of the invention, the preferred concentration of test compound is between 1 μM and 500 μM. A preferred concentration is 10 μM to 100 μM. In some preferred embodiments, it is desirable to use a series of dilutions of test compounds.

In some embodiments of the invention, the preferred range of time and temperature for the assay is 1–10 hours at 30°–37° C. Preferred temperature and amount of time for the assay are 30° C. for 0.5–1 hour when using p56$^{RB}$. Preferred temperature and amount of time for the assay are 30° C. for 8 hour when using MBP.

According to the method that is the invention, the level of phosphorylation activity in the test assay is determined by removing measuring the level of radioactive phosphorous attached to the substrate p56$^{RB}$. In preferred embodiments, the amount of labelled phosphorous that is bound to substrate is measured with scintillation counter.

The present invention relates to kits and reagents for performing the assay. Kits include one or more containers having contents selected from the group of reagents: PITALRE immunocomplexes; antibodies useful to isolate PITALRE immunocomplexes; [gamma$^{32}$P]ATP; p56$^{RB}$; MBP and casein. Kits may also include instructions and controls such as known inhibitors. For example, anti-PITALRE antibodies that inhibit PITALRE activity may be provided as controls. Kits may also include instructions for carrying out assays and interpreting data to identify compounds that are inhibitor candidates.

The invention relates to methods of identifying compounds that enhance PITALRE activity. Such methods kits and reagents are as described above except that test compounds are identified as enhancer candidates if, in the test assay, the increase the level of phosphorylation relative to control. The kits, with instructions for analyzing data to identify enhancer candidate compounds, and reagents of the invention may be used in this method.

The present invention is further illustrated by the following examples, which are not intended to be limiting in any way.

EXAMPLES

Example 1

With the aim of isolating additional putative controllers of the mammalian cell cycle, a combination of PCR amplification and low-stringency screening of a human cDNA library was performed. By using this strategy, a CDC2-related protein kinase, temporarily named PITALRE for the characteristic motif Pro-Ile-Thr-Ala-Leu-Arg-Glu (SEQ ID NO:7) was isolated and characterized. Its subcellular localization was determined, several associated proteins were identified, and kinase activity in its immunocomplexes was demonstrated. The regulation of this kinase activity during the cell division cycle was investigated. These studies define an additional protein kinase that may be involved in cell cycle control or in differentiation of specific cell types.

Materials and Methods cDNA Cloning

Two degenerate oligonucleotides were used in the polymerase chain reaction (PCR) to amplify ≈500-bp fragments related to the cdc2 family of genes. A mouse embryonic cDNA library was used as a source of cDNA. The 5' oligonucleotide (5'-GCAGGATCCGARAARATYGGNGARGGNACNTA-3' (SEQ ID NO:8-5'-GCAGGATCCGA(GA)AA(GA)AT(TC)GG(GATC)GA(GA)GG(GATC)AC(GATC)TA-3' ) ) corresponds to the CDC2 region of amino acid sequence Glu-Lys-ile-Gly-Glu-Gly-Thr-Tyr (SEQ ID NO:9) and the 3' oligonucleotide (5'-CGGCTGCAGARNAYYTCNGGNGMNCKRTAC CA-3' (SEQ ID NO: 10-5'-CGG CTGCAGA(GA)(GATC)A(TC)(TC)TC(GATC)GG (GATC)G(AC)(GATC)C(GT)(GA)TACCA-3')) corresponds to the CDC2 region of amino acid sequence Trp-Tyr-Arg-Ser-Pro-Glu-Val-Leu (SEQ ID NO:11) (R=G or A, Y=T or C, N=G, A, T, or C, M=A or C, and K=G or T). PCR was carried out for 25 cycles (1 min at 94° C., 2 min at 55° C., and 3 min at 72° C., followed by a final 8-min incubation at 72° C.) following manufacturer directions (Perkin-Elmer/Cetus). The nucleotide sequence of several fragments was determined. With one of these cdc2-related PCR-amplified fragments as a probe, a human CEM cDNA library (in Lambda ZAP II; Stratagene) was screened at low stringency (38% formamide containing 0.1% SDS, 150 μg of herring sperm DNA per ml, 5× Denhardt's solution (1×=0.02% polyvinylpyrrolidone/0.02% Ficoll/0.02% bovine serum albumin), and 5×SSPE (1×=0.18M NaCl/10 mM phosphate, pH 7.4/1 mM EDTA). Hybridization was performed at 37° C. for 16 h, and low-stringency washes were carried out at 37° C. for 20 min in 0.30M NACl/0.030M sodium citrate, pH 7/0.1% SDS. Two positives contained≈1.4-kb (PK10) and ≈1.5-kb (PK14) inserts. Double-stranded DNA sequence determination was performed by using Sequenase 2.0 (United States Biochemical) and oligonucleotide primers Comparison of the sequences with the major data bases showed that the clone of 1.4 kb corresponded to the PSK-J3/CDK4 and the clone of 1.5 kb encoded a previously unknown CDC2-related putative kinase.

Biological Reagents

The coding region of clone PK14 starting at nucleotide 65 was PCR-amplified and subcloned in pGEX-2T (Pharmacia) linearized with BamHI/Sma I. Bacterially expressed glutathione S-transferase (GST)-PITALRE fusion protein was used to immunize rabbits. Positive rabbit serum was affinity-purified with GST and GST-PITALRE columns. Preparation of anti-C-terminal peptide antibodies to CDC2 (G6) and CDK2 were perfromed by well known means.

Cell Culture and Biological Assays

Cells were obtained from the American Type Culture Collection. Cell culture, cell labeling, and centrifugal elutriation were performed by well known methods. HeLa cells were synchronized by serum deprivation and hydroxyurea treatment. Flow cytometric analysis was performed with an Epics Elite system (Coulter). Nuclei from HeLa cells were obtained. Immunoprecipitations were performed. Immunoprecipitation-reprecipitation experiments and V8 partial digestion mapping were performed using well known methods. Enhanced chemiluminescence (ECL; Amersham) was used in immunoblot experiments. Kinase assays from immunoprecipitated complexes were performed at 30° C. for 20–30 min in 20 mM Hepes/10 mM magnesium acetate/1 mM dithiothreitol/10–100 µM ATP/5 µCi (1 µCi= 37 kBq) of [$\gamma^{32}$P]ATP (DuPont) containing 1–5 µg of the following substrates: myelin basic protein (MBP) and casein (Sigma), histone H1 (Boehringer Mannheim), p56 retinoblastoma (RB) bacterially expressed protein, and several GST fusion proteins (total volume, 25 µl).

Results and Discussion

Isolation of a Human cDNA Encoding an Additional Member of the CDC2 Family of Protein Kinases With the aim of isolating new members of the CDC2 family of serine/threonine protein kinases, cDNA from a mouse embryonic library was PCR-amplified by using degenerate oligonucleotides. Next, a unique PCR clone was used as a probe to isolate two human cDNAs. One of them was PSK-J3, which recently has been renamed CDK4 because of its association with the D-type cyclins. The second cDNA was found to be 1461 bp long and contained an open reading frame of 1181 bp. A putative start site for translation was found at nucleotides 65–67. Starting at this methionine, the predicted translation product is a 372-amino acid protein with an expected relative molecular mass of ≈43 kDa. The 3' noncoding region does not contain a poly(A) tail. The deduced amino acid sequence contains the 11 conserved regions characteristic of the protein kinase catalytic domain, and the putative. ATP-binding site is identical to that of SGV1, a putative kinase required for a guanine nucleotide-binding protein α subunit-mediated adaptive response to pheromone in *S. cerevisiae*. A PSTAIRE (Pro-Ser-Thr-Ala-Ile-Arg-Glu (SEQ ID NO:12)-like motif, PITALRE, is found at residues 60–66 that is also closely related to the motifs of SGV1 and CHED. This protein was tentatively named "PITALRE," until more functional information allows for more precise classification. PITALRE has the two regulatory threonine residues corresponding to positions 14 and 161 in CDC2, but as in SGV1, the residue corresponding to Tyr-15 of CDC2 is not conserved, thus suggesting an alternative mode of regulation. PITALRE is 47% identical to CHED, a human homolog of CDC2 required in hematopoiesis. PITALRE shares ≈41–43% identify (61–65% similarity) with the *S. cerevisiae* SGV1 kinase and the human CDC2, CDK2, CDK3, and CDK5 kinases, but, as mentioned above, certain amino acid clusters are better conserved in relation to SGV1. The protein also contains short extensions at the amino- and carboxyl-terminal ends that may have specific regulatory functions, such as substrate recognition or subcellular localization.

Expression of PITALRE in Human Tissues

To determine whether PITALRE is also a tissue-specific kinase, RNA (Northern) blot experiments were performed. At least two transcripts of ≈2.8 kb and ≈3.2 kb are observed in all tissues tested, which indicates that PITALRE expression is ubiquitous. However, PITALRE expression is highest in liver and placenta, which suggests that PITALRE may be involved in specialized functions in certain cell types. Similarly, high levels of CDK5 have been detected in neurons, cells no longer in the cell cycle; on the other hand, CDK5 associates with the D-type cyclins and with proliferating cell nuclear antigen, which paradoxically suggests a $G_1$ cell cycle function. Moreover, other transcripts of higher molecular mass can be detected in some tissues. This may be due to the presence of partially processed RNA or alternative splicing or to the existence of related genes. The difference in size between the RNA transcripts and the ≈1.5-kb PITALRE cDNA is probably due to the presence of long 5' and/or 3' extensions and/or the poly(A) tail.

Affinity-Purified Antibody Recognizes a Cellular Protein of ≈43 kDa

To identify the cellular protein encoded by the PITALRE cDNA, immunoprecipitation/reimmunoprecipitation experiments were performed. Affinity-purified anti-PITALRE antibodies recognized directly a single polypeptide of ≈43 kDa, and no other cross-reacting bands were observed. The ≈43-kDa band was detected in immunoprecipitates of lysates from many cell lines at similar levels, including ML-1, CEM, HeLa, WI38, Col. 38,293, SAOS-2, and WERI cells, which is consistent with ubiquitous expression immunoblots of affinity-purified anti-PITALRE immunoprecipitates also showed a band of 43-kDa. To determine whether or not the PITALRE cDNA encodes a full-length protein, we transcribed in vitro the cDNA and translated the cRNA in a rabbit reticulocyte lysate in the presence of [$^{35}$S]methionine. The in vitro synthesized polypeptide had the expected molecular mass and was immunoprecipitated specifically by the affinity-purified antibody. To demonstrate that the in vitro translated product and the protein immunoprecipitated by the antibody from $^{35}$S-labeled cell lysates were the same polypeptide, partial digestion was performed with V8 protease from the excised bands. The pattern of the V8 partial digestion was identical.

The ability of the PITALRE antisera and the affinity-purified antibodyto recognize related polypeptides was tested using in vitro translated proteins. PITALRE antibodies were not able to immunoprecipitate in vitro translated CDC2, CDK2, CDK4, and CDK5. This observation, together with the immunoprecipitation/ reimmunoprecipitation experiment, indicates that the anti-PITALRE antibodies are specific and suitable for the biological characterization of PITALRE function. On the other hand, to immunoprecipitate in vitro translated PITALRE we used several antibodies raised against members of the CDC2 family of protein kinases: G6, GS, anti-PSTAIRE, and antiCDC2-CT antibodies against CDC2; C-terminal CDK2, CDK3, CDK4, and CDK5 anti-peptide antibodies; and antiERK1 and anti-ERK2. Only anti-PSTAIRE antibodies were able to immunoprecipitate this polypeptide.

Subcellular Localization of PITALRE

To gain additional circumstantial evidence as to the physiological role of PITALRE in cells, its subcellular location was determined by subcellular fractionation followed by Western blotting. PITALRE is primarily, if not exclusively, a nuclear protein. The PITALRE primary sequence contains a putative nuclear localization signal which agrees with the consensus sequence present in many nuclear proteins. Similar signals were found in the CHED- and PCTAIRE-type kinases, but their subcellular localization is still unknown.

PITALRE-Associated Proteins

The activity of the CDC2 and CDC2-related protein kinases is regulated by phosphorylation and by association with cyclins. The kinases that interact physically with cyclins are called CDKs. Some of these kinases are also known to associate with the tumor suppressor gene product pRB or the related protein p107. To search for known or unknown proteins that associate with PITALRE, immunoprecipitations of $^{35}S$ labeled cell lysates was performed. Three proteins with molecular masses of $\approx 155$, $\approx 95$, and $\approx 80$ kDa were coimmunoprecipitated with PITALRE. The absence of these proteins in the immunoprecipitation/ reimmunoprecipitation experiment and in the immunoblot indicates that they are associated and are not cross-reacting proteins. These associated polypeptides are not any of the known cyclins including cyclin X.

PITALRE-Associated RB Protein Kinase Activity

To investigate further the function of this putative kinase, the kinase activity associated with its immunocomplexes was determined. PITALRE immunocomplexes showed a strong $p56^{RB}$ kinase activity. The immunocomplexes also phosphorylated MBP and casein, but at a lower level than when the $p56^{RB}$ was used as a substrate. Interestingly, histone H1 was not phosphorylated, which suggests that the site of phosphorylation is different from that recognized by CDC2 and CDK2. This observation suggests that all three of these kinases may regulate target molecules through phosphorylation in non-overlapping signal transduction networks. Other exogenous substrates, including CDKs and cyclins, were not phosphorylated. The associated kinase activity was also able to phosphorylate PITALRE and its associated proteins, which suggests that these proteins may be substrates of the PITALRE kinase. The identity of PITALRE, which runs slightly slower in the SDS polyacrylamide get, was confirmed by reimmunoprecipitation.

CDC2 and CDK2 kinases have a cell cycle-regulated kinase activity that can be monitored by using different exogenous substrates. To examine whether or not PITALRE shares this cell cycle-modulated behavior, in vitro kinase assays of PITALRE immunocomplexes during the cell cycle were performed. After serum deprivation and blocking with hydroxyurea, cells were allowed to progress through the cell cycle in a synchronous fashion. Cell fractions were lysed, and the protein extracts were immunoprecipitated with affinity purified anti-PITALRE to determine the kinase activity towards $p56^{RB}$ exogenous substrate. Phosphorylation of RB protein during the $G_1$ phase of the cell cycle occurs at several different sites. The presence of specific sites for different kinases suggests a multifactorial regulation of this protein. The lack of regulation throughout the cell cycle when RB protein is added as exogenous substrate does not necessarily mean that PITALRE is not involved in the mechanisms controlling cell cycle regulation of RB protein. CLN3, a $G_1$ cyclin from S. cerevisiae does not change in abundance during the cell division cycle, and its associated kinase activity also remains invariant.

Example 2

Materials and Methods cDNA cloning

Two degenerate oligonucleotides were employed in the Polymerase Chain Reaction (PCR) to amplify ~500 bp fragments related to the cdc2 family of genes by using DNA isolated from a mouse embryonic cDNA library as a template. The 5' oligonucleotide (5'-GCAGGATCC GARAARATYGGNGARGGNACNTA-3' (SE Q ID NO:8–5'-GCAGGATCCGA(GA)AA(GA) AT-(TC)GG (GATC)GA(GA)GG(GATC)AC(GATC)TA-3')) corresponds to the CDC2 region of amino acid sequence EKIGEGTY (SEQ ID NO:13) and the 3' oligonucleotide (5'-CGGCTGCAGARNAYYTCNGGNGMNCKRTA CCA-3' (SEQ ID NO:10–5'-CGGCTGCAGA(GA) (GATC) A(TC) (TC)TC(GATC)GG (GATC)G(AC)(GATC)C(GT) (GA)TACCA-3')) corresponds to the CDC2 region of amino acid sequence WYRSPEVL (SEQ ID NO:14). The PCR reactions contained 5 µM of each primer, 200 µM each dNTP, 10 mM Tris-HCl pH 8.3, 50 mM KCl, 1.5 mM $MgCl_2$. 0.001% gelatin, and 2.5 U of Taq polymerase (Cetus). PCR was carried out for 25 cycles (1 min at 94° C., 2 min at 55° C., 3 min at 72° C.) followed by a final 8 min incubation at 72° C. PCR products were gel purified, digested with BamHI/PstI and subcloned in pUC18. The nucleotide sequence of several fragments was determined. One of the cDNAs encoded a novel putative PSTAIRE-like protein kinase. This cDNA was labeled by random primer and used to screen a human cDNA library made from HeLa cells (Lambda-ZAP 11, Stratagene). Screening was performed on 2×106 recombinant phages it low stringency (38% formamide, 5× Denhart's solution, 5× SSPE, 0.1% SDS, and 150 jig/ml herring sperm DNA). Hybridization was performed at 37° C. for 16 h, and low stringency washes were carried out at 37° C. for 20 min in 2× SSC, 0. I% SDS. The positive lambda-phages were purified and the in vivo bluescript (Stratagene) excision was performed. Double strand DNA sequence was performed by using the dideoxy chain termination method utilizing Sequenase 2.0 (United States Biochemical Corp.) and oligonucleotide primers. To isolate full length clones we performed screenings of lambda-ZAP II cDNA libraries from human HeLa and CEM cells (Stratagene), and 293 cells. These screenings were performed at high stringency (50% formamide, 5× Denhart's solution, 5× SSPE, 0.1% SDS, and 150 µg/ml herring sperm DNA). Hybridization was performed at 42° C. for 16 h, and three washes were carried out at 42°–50° C. for 20 min in 0. I×SSC, 0. I% SDS.

Rapidamplification of cDNA ends (RACE) ClontechRACE kit was used following manufacturer directions.

The oligonucleotide 5'-GTGCAGATACTGGAGGCCCCGGAG-3' (SEQ ID NO:15) was used to reverse transcribe poly-(A+) RNA purified from Hela cells by using oligo-dT magnetic beads (Promega). The nested oligonucleotide 5'-CTC CTCGAGTGACCTGAGCCTCCGAGAAGGGTG-3' (SEQ ID NO:16) which contains a tail with a XhoI restriction site for subcloning purposes, was used in the PCR reactions. After 45 cycles of amplification a band of ~450 bp was detected, gel purified, digested with EcoRI/XhoI, and subcloned in pBluescript (Stratagene).

Northern blot analysis

Two adult and one fetal human tissue blots from Clontech were used. Each lane contained 2 jig of poly-(A)+RNA. An α-dCTP random primer labeled cDNA probe (nt 1–419) was used for the blot hybridization following the manufacturer's directions.

Plasmids pGEX-2T-PK2JV1 and pGEX-2T-PK2JV2 were constructed by PCR using the 5' olignucleotides 5'-CTC GGATCCGGAATTCCCGTATTCCTGGGACGATGC-3' (SEQ ID NO:17), and 5'-CTC GGATCCGGAATTCCCGTGAAGGAGTTTGAGAAG-3' (SEQ ID NO:18) respectively, and the common 3' oligonucleotide 5'-CAGGAATTCCGGAGTCCTGCCAGGC-3' (SEQ ID NO:19). The amplified products were digested with either BamHI or EcoRI and subcloned into the PGEX-2T vector. pBSPK2JV1 and pBS-PK2JV2 were obtained by digesting pGEX-2T-PK2JVI and pGEX-2T-PK2JV2 with BamHI and subcloning the released inserts in the pbluescript vector (Stratagene). pBS-PK2JT7 was obtained by digesting. pBS-PK2J with EcoRI and subcloning the released insert into pbluescript (selection of correct orientation was carried out by restriction mapping). pBS-PK2japaI was obtained by subcloning the ApaI restriction fragment of PK2J into pbluescript.

Recombinant Expression in Bacteria

Expression of the fusion protein was performed using well known methods. 100 μCi of $^{35}$S-Met were added the last 20 min of IPTG induction. After expression, bacteria were harvested and soluble protein was extracted in 20 mM tris-HCl, 100 mM NaCl, 1 mM EDTA, 0.5% NP-40, 10 μg/ml leupeptin, and 100 μM PMSF by sonication. insoluble protein was extracted in the same buffer containing 2% sarkosyl. Purification and fusion protein elution and cleavage were carried out as by well known methods. (1989).

Antibodies

Preparation of specific anti-C-terminal peptide antibodies to CDC2 (G6) and CDK2 have been described; polygonal anti-S. pombe CDC2 (C, 8) and C-terminal CDK4 and CDK5 anti-peptide antibodies were a generous gift of Y. Xiong and H. Zhang; and, anti-PSTAIRE, -ERKI-III, and -CDC2-CT were generously supplied by S. Pelech. Anti-PITALRE antibodies were obtained by standard methods.

"In vitro" Transcription and Translation

Translation was performed in vitro using the TNT rabbit reticulocyte lysate kit (Promega) with 35S-Met (translation grade, Dupont). In vitro translated proteins were immunoprecipitated using the antibodies.

Results and Discussion

Cloning of PISSLRE cDNAs

Two degenerate oligonucleotides were synthesized based on the high degree of identity between the deduced amino acid sequences of CDC2 and CDK2 from different species. The 5' oligonucleotide corresponded to the amino acid sequence EKIGEGTY (SEQ ID NO:13) from the conserved region I and the 3' oligonucleotide corresponded to the amino acid sequence WYRSPEVL (SEQ ID NO:14) from the conserved region VIII (Hanks et al, 1988). The polymerase chain reaction (PCR) technique was employed to amplify ~500 bp cDNA fragments containing CDK-related sequences using as a template DNA isolated from a mouse embryo cDNA library. The gel-purified DNA was subcloned in the pUC18 vector. From the analysis of the sequence of several clones, two CDK-related cDNAs were identified (PCR-M1 and PCR-M2). The deduced amino acid sequence revealed that PCR-M1 was PSSALRE. PSSALRE has been shown to be associated with D-type cyclins, and since then, called CDKS. PCR-M2 encoded a novel putative CDC2-related protein kinase, which contained the conserved PSTAIRE-like motif (PISSLRE). This mouse cDNA as a probe was used to screen a human cDNA library prepared from human HeLa cells. This screening was performed at low stringency because the probe and the cDNA library came from different species, and because of the possibility of identifying other CDC2-related family members. From this screening, a cDNA clone (PK3A) was isolated which displayed a high degree of identity with the PCR-amplified mouse cDNA (87%). The PK3A cDNA was ~1.6 kb long and contained a poly-(A+) tail. The amino acid sequence encoded by PK3A contained a "spacer region" of 70 hp in conserved domain VII that, although present in the deduced amino acid sequence of the mouse clone, was not present in other CDK protein kinases. Further analysis of the corresponding cDNA region revealed a change in the codon frame in this region. Moreover, a careful reading of the cDNA sequence showed putative consensus sites for introns in the flanking regions of this "spacer", in both, the human (GT- 66nt -AG) and the mouse (GT- 30nt -AG) cDNAs. In addition, the putative mouse intronic sequence was shorter than the human and the nucleotide sequence was only conserved in the flanking regions.

Since the clone PK3A was not full length and because of the presence of putative introns, we re-screened the same CDNA library using an ~400 bp 5' cDNA restriction fragment of PK3A as a probe. From this second screening, several clones encoding partial PISSLRE-containing polypeptides were isolated. Partial sequence of the positive clones obtained revealed that the most 5' clone (PK1B) encoded a polypeptide with an amino terminal sequence extending further than any of the other known CDKs. However, no typical initiation sites were found upstream of the conserved ATP binding site. From this same screening, a clone (PK2B) was obtained which, although shorter than PK3A, did not contain the "spacer" region. Sequence alignment of the two clones confirmed the presence of intron-initiation and -termination consensus sequences flanking the cDNA "spacer" in PK3A. Additionally, another putative intronic sequence of 33 hp was found in the PK3A cDNA sequence. Alignment of PK2B and several CDK sequences did not show any "spacer" regions indicating that clone PK2B was free of intronic sequences. Two additional human libraries (made from human 293 and CEM cell lines) were screened seeking full length clones. From the screening of the CEM library, a clone termed PKCB1 was isolated which, although longer than PKIB, did not contain any putative ATG-initiation site.

Next, the Rapid Amplification of cDNA Ends (RACE) was performed by using poly-(A+) RNA obtained from HeLa cells. By using this method, cDNA bands of ~50 bp were amplified. Sequence alignment of seven independent clones showed that their 3' terminal-end sequences matched with the clone PK2B. There was some slight variation in the length of the clones (410±10 bp) with the exception of one that contained an intronic region. This intron was also observed in clones PKIB and PKCB1. The different length at the 5'-terminal end of the RACE-obtained clones indicates that they have arisen from different reverse transcribed cDNAs. In addition, a single point mutation was detected in only one of these seven independent clones, making the presence of identical mutations in all the clones unlikely. The longest RACE clone (RACE2) was ligated to PK2B by using their common BstXI site. The resulting clone was renamed PK2J and was 1424 bp long. An open reading frame starts at nt 82, just downstream of a stop codon. Comparison of the deduced amino acid sequences of PK2J and the DNA sequences present in the GeneBank/EMBL data bases showed the highest score of identity with p58/GTA. The first identical amino acid corresponds to nt 100–102 of PK2J and no typical initiation sites are found between this amino acid and the immediately upstream stop codon, which indicates that translation should start at a non-AUG codon. Two candidate initiation codons are found in frame, a GTA codon (nt 85–87) and a CTG codon (nt 91–93). In addition, a GTG codon (nt 109–111) is found at the same position where CDC2, CDK2, CDK3, and CDK5 contain their initiation sites. However, the presence of identity between p58/GTA and the protein encoded by PK2J upstream of this codon suggests that it is not the initiation site.

Structure of the PISSLRE Encoded Protein

Starting at nucleotide 85, the predicted translation product is a 316 amino acid protein with an expected relative molecular mass of ~35.8 kDa. The deduced amino acid sequence of PK2J contains the hallmarks of a protein kinase, including the XI conserved regions and a PSTAIRE-like sequence, PISSLRE (following conventional guidelines, this characteristic motif will name this kinase until more functional characterization is available). The PISSLRE protein kinase is ~55% identical to p58/GTA, a protein kinase which associates to the galactosyl transferase protein. Overexpression of p58/GTA in CHO cells inhibits the entry into the S phase of the cell cycle, which suggests an involvement of this kinase in the cell cycle regulatory machinery. PISSLRE is also 38–45% identical to the members of the CDK family of protein kinases. This putative kinase has a threonine and a tyrosine within the putative ATP binding site at residues 22 and 23, respectively. These residues have been shown to negatively regulate the activity of the CDC2/CycB complex and are conserved in most of the members of the CDK family of protein kinases. PISSLRE also contains the conserved threonine residue corresponding to the regulatory threonine 161 from CDC2. Phosphorylation of this residue in CDC2 activates its kinase activity.

PISSLRE Expression in Human Tissues

Northern blot analysis was performed to test the expression of the PISSLRE gene in various human tissues. Two major bands of 1.7 and 3.6 kb can be detected in all adult tissues. The length of the faster transcript is in agreement with the length of the cDNAs. The slower band may represent unprocessed RNA, which would explain the high number of cDNA clones obtained containing introns.

The levels of expression of PISSLRE in fetal tissues appear to be lower than in adult tissues. Moreover, expression of PISSLRE in lung, liver and kidney is higher than in brain and heart in both adult and fetal tissues. Interestingly, PISSLRE is expressed in tissues which contain high percentage of terminally differentiated cells, which are withdrawn from the cell cycle. In this context, PISSLRE resembles CDK5, a kinase which is found to complex with D-type cyclins and with the proliferating cell nuclear antigen. The association of CDK5 with proteins involved in the cell cycle progression is in contrast with the high levels o expression of CDK5 in neurons, cells no longer dividing.

Characterization of the PISSLRE-polypeptide

To analyze the PISSLRE protein, the PK2J cDNA was transcribed/translated in vitro. Three major polypeptides (26, 29 and 32 kDa) were obtained when transcription was directed by the T3 RNA polymerase. The 26 and 29 kDa polypeptides appeared to correspond to initiation of translation at the internal methionine residues. To ascertain the nature of the 32 kDa protein, a series of deletion mutants were constructed which were subcloned in the bluescript vector. The 32 kDa polypeptide was present in the original construct (T3 RNA polymerase). However, it was not clearly present in either the same construct subcloned in the opposite direction (T7 RNA polymerase) or the rest of deletion mutants. The full length clone and the V1 and V2 deletions (T7 RNA polymerase) showed a shadow of bands of different molecular mass between 29 and 32 kDa. The presence of the 29 kDa polypeptide in PK2JapaI, but not in the PK2B in the in vitro translations, further indicates the initiation of the 26 and 29 kDa polypeptides at the two internal ATG sites. To produce full length polypeptides initiated at valines 1 and 2, we subcloned deletions V1 and V2 in the PGEX-2T vector. GST fusion proteins were produced in the presence of $^{35}$SMet and cleaved with thrombin. Bands corresponding to the GST moiety and the PISSLRE polypeptides were observed. The length of the PISSLRE polypeptide from the GST-V2 construct, which contains two additional amino acids due to subcloning design, was very close to the 32 kDa band obtained by using the PK2J construct, which appears to be also present as a faint band in the PK2JV2 in vitro translation products. This data may indicate that translation could start at the GTG codon (nt 109–111) which is in contrast with the amino acid sequence identity between PISSLRE and p58/GTA found upstream of this codon. The nature of the exact position of the initiation site will remain obscure until cellular PISSLRE is isolated.

Several immunological reagents have been generated to different members of the cdc2 family of protein kinases. Some of these reagents cross-react within subfamilies of these kinases. To test whether or not PISSLRE is recognized by some of these reagents, we used in vitro translated PISSLRE in immunoprecipitation experiments. The in vitro translated PISSLRE. was obtained by using, both T3 and T7RNA polymerases. The following antibodies were used: GS, G6 anti-CDC2-CT, and anti-PSTAIRE antibodies to CDC2; C-terminal CDK2, CDK4, and CDK5 anti-peptide antibodies; anti-ER1-III; and, anti-PITALRE. None of these antibodies was able to specifically immunoprecipitate PISSLRE polypeptides.

In the past few years, there has been an explosion in the identification of related members of different families of proteins, such as kinases, cyclins, transcription factors, phosphatases etc. Thus, it seems to be that in higher eukaryotes, very specialized protein complexes similar in structure may work in different pathways or at various levels in a specific pathway cascade. An example of that may be the different Cyclin/CbK complexes working one upstream of the other in the same pathway. This is the case of the CDC2-related kinase CAK/p40$^{MO15}$, which regulates the activity of CDK/cyclin complexes. The identification and functional characterization of all partners involved in these critical pathways will allow the design of drugs that will permit one to either block or bypass the "out of control functions" of specific protein complexes in certain disease states and lead to the restoration of normal functions.

Example 3

Orderly progression through the cell cycle requires sequential activation and inactivation of cyclin-dependent kinases (cdks). This is achieved in part through the association of cdks with positive regulators called cyclins and inactivation of cyclin-cdk complexes by a rapidly growing number of cyclin-cdk inhibitors. Recently, the role of cell cycle control proteins both as primary effectors and as mediators of tumorigenesis has become a subject of increased interest.

As a first step in investigating the possible involvement of cdc2 related kinases and cdk inhibitors in human tumors, a rodent-human hybrid panel was screened for the presence of these genes to determine the chromosomal locations of cdk3, cdk6, PISSLRE, PITALRE and p27. The regions where the genes were mapped on the chromosomes were examined to determine if such chromosomal regions may be altered in human tumors and the possible involvement of the genes in some of these malignancies. The regions where the genes for these proteins map were analyzed to determine correlation to chromosome regions involved in loss of heterozygosity (LOH) in breast and other tumors.

Materials and Methods

Rodent-human Hybrids

Hybrid DNAs were from previously described rodent-human hybrid cell lines (Huebner, K. et al. AM. J. Hum. Genet., 48:726–740, 1991; Huebner, K., et al. Hum. Genet., 91:217–223, 1993; and LaForgia, S., et al. Proc. Natl. Acad. Sci. USA, 81:5036–5040, 1991, which are each incorporated herein by reference) or from the Human Genetic Mutant Cell Repository (HGMCR, Coriell Institute, Camden, N.J.).

PCR Amplification

PCR amplification was carried out on 100 ng of genomic DNA from human placenta, mouse, hamster, and rodent-human hybrids with 300 ng each of forward and reverse primer. Thirty cycles of amplification were carried out as follows: 94° C. 30 sec; 60° C. 30 sec; 72° C. 30 sec. PCR products were separated in 1.5% agarose gels, denatured, neutralized and transferred to Hybond-C nylon membranes (Amersham). Filters were processed as described below. For each gene to be mapped, several primer pairs were tested on human, mouse and hamster DNA in order to obtain a human specific amplification product of the expected size which hybridized with the appropriate oligonucleotide or cDNA probe. Forward primers were given odd numbers and reverse primers were given even numbers. Oligonucleotide primers used for amplification were:

03cdk6, 5' ACCTCGGAGCTGAATACA 3' (SEQ ID NO:20);

04cdk6, 5' TTCCTTGGAGAAGCAGAG 3' (SEQ ID NO:21);

01p27, 5' GTGGACCACGAAGAGTTA 3' (SEQ ID NO:22);

02p27, 5' CTCTTGCCACTCGTACTT 3' (SEQ ID NO:23);

01PIS, 5' ACATCCTCCACTGACTTC 3' (SEQ ID NO:24);

02PIS, 5' TCCCAAGAAGCAGTGGTT 3' (SEQ ID NO:25);

01PIT, 5' TTGCCACTAGGGCTCTTG 3' (SEQ ID NO:26);

02PIT, 5' CAGCAAGGACAAGACA 3' (SEQ ID NO:27).

Southern Blotting

DNA was isolated from rodent-human hybrids, mouse and hamster cell lines and CLL tumor samples by standard phenolchloroform extraction. Restriction enzymes (Boehringer Mannheim) were used to digest 10 µg of DNA for rodent-human hybrid Southern blots and 5 µg of DNA for Southern blots with tumor samples. Human placenta DNA (ONCOR) was used as a positive control. Digested DNA was size fractionated by gel electrophoresis in 0.7% agarose for 16 hr at 22 V, depurinated, denatured, and vacuum transferred onto Sure Blot nylon membranes (ONCOR) following Probe Tech 2 manufacturer's instructions (ONCOR). After transfer membranes were baked for 1 hr at 80 C. and prehybridized in 5× Saline-sodium phosphate-EDTA (SSPE), 5× Denhardt's, 1% SDS, 0.1 µg/ml salmon sperm DNA solution at 65° C. for 1 hr. Filters were hybridized for 16 hr at 65 C. using approximately 5×10$^6$ cpm/ml hybridization solution. Filters were then washed at 65° C. sequentially in 2× Saline-sodium citrate (SSC)-0.1% Sodium Dodecyl Sulfate (SDS) for 30 min; 0.2× SSC-0.1% SDS for 20 min; and 0.1× SSC-0.1% SDS for 10 min. Finally, filters were exposed to Kodak X-Omat AR film with two DuPont Cronex Lightning-plus intensifying screens at −70° C. for 16 or 96 hrs.

cDNA Probes

Complementary DNA (cDNA) probes for cdk2, cdk3, cdk4, MDM2, and p27 which were used in this study were graciously provided by the laboratories involved in the cloning and characterization of these genes (Meyerson, M., et al. EMBO Journal, 11:2209–2917, 1992; Oliner, J. D., Nature, 358:80–83, 1992; Polyack, K., et al. Cell, 78:59–66, 1994; Tsai, Li-H., et al. Nature, 353:174–177, 1991; and Xiong, Y., et al. Cell, 71:504–514, 1992, which are each incorporated herein by reference). The cDNA probes for PISSLRE and PITALRE were cloned as described in (Grana, X., Oncogene 9:2097–2103, 1994 and Grana, X., Proc. Natl. Acad. Sci. USA, 91:3834–3838, 1994, which are both incorporated herein by reference). cDNA inserts for use in hybridization experiments were excised from vector DNA by digestion with the appropriate restriction enzyme and radiolabelled by random priming to a specific activity of 10$^8$–10$^9$ cpm/µg using the Prime it II kit (Stratagene).

Oligonucleotide Probes

The following probes were used.

05cdk6, 5' TGATCCTGCGGAGAACACCCTTGG 3' (SEQ ID NO:28) and

05p27, 5' ACTGCAGAGACATGGAAGAGGCGA 3' (SEQ ID NO:29)

These oligonucleotides, which hybridize to sequence internal to the expected amplification products for cdk6 and p27, respectively, were used to probe Southern blots of PCR amplified gene fragments. Oligonucleotides were end-labeled with polynucleotide kinase (Boehringer Mannheim) following standard procedures. Hybridization and washing of PCR Southern blots was carried out as for genomic blots. PCR filters were exposed to X-ray film for 30 min at room temperature.

Results

A panel of twenty rodent-human hybrids retaining individual chromosome, and human and rodent control DNAs were tested by Southern blot or PCR amplification for the presence of human cdk3, cdk6, PISSLRE, PITALRE or p27 gene sequences. Regional localization of each gene within the assigned chromosome was then achieved by testing a small panel of rodent-human hybrids retaining defined subregions of the relevant chromosome.

To determine the chromosome location of the cdk3 gene, DNAs from the hybrid panel were digested with EcoRI, electrophoresed, transferred and hybridized to the cdk3 cDNA. The cdk3 gene was present only in hybrids retaining human chromosome 17. Hybrids were used to further localize the cdk3 gene to 17q22-qter. The cdk3 locus is telomeric to the recently identified BRCA1 gene (Miki, Y., et al. Science, 266: 66–71, 1994). Two distinct regions of LOH telomeric to the BRCA1 locus have been described in breast cancer (Cropp, C. S., et al. Cancer Res., 53:5617–5619, 1993). In order to investigate the possible involvement of the cdk3 gene in breast cancer; several breast cancer cell lines known to carry LOH at 17q were examined by Southern blotting to identify alterations of the gene. No evidence of cdk3 deletion was found. However, preliminary data indicates the presence of a cdk3 rearrangement or polymorphism in the MDA-MB-543 breast cancer cell line. Abnormal bands in MDA-MB-543 DNA were detected with two of eight enzymes tested.

The chromosomal location of the loci for each of cdk6, PISSLRE, PITALRE, and p27 was determined by screening individual hybrid DNAs from the hybrid mapping panel for the presence of a specific PCR amplified product of the expected size using oligonucleotide pairs specific for each gene sequence. In order to increase specificity, primers were sometimes selected within 3' or 5' untranslated regions of available cDNA sequences. When untranslated regions were not suitable for primer design, primers were chosen within the least conserved regions of the cDNAs. The same oligonucleotide pairs were then used to sublocalize these genes to specific regions within assigned chromosomes. The specificity of amplified PCR products was confirmed by hybridization to cDNA (PISSLRE and PITALRE) or oligonucleotide probes (cdk6 and p27). The regional localization of each of the genes was determined: cdk6 at 7p13-cen; PISSLRE at 16q24; PITALRE at 9q34.1; and p27 at 12p13.

Chromosome 12 numerical abnormalities are associated with a variety of human tumors. In particular, trisomy 12 has been associated with a high percentage of chronic lymphocytic leukemia (CLL) and ovarian tumors. Trisomy 11 in ALL has been shown to represent a masked rearrangement of the ALL-1 gene involved in translocations of chromosome 11 at band q23 characteristic of acute leukemias. In order to determine whether a similar phenomenon resulting in activating rearrangements of putative oncogenes (cdk2, cdk4, and MDM2) located on chromosome 12 or in the production of dominant negative forms of the cyclin-cdk inhibitor p27, might be occurring in CLL, more than twenty DNAs from randomly selected CLL patients were examined by Southern blotting with cDNA probes for cdk4, cdk2, MDM2, and p27. No evidence of rearrangement for p27, cdk4 or MDM2 was found in Southern blots of CLL tumor DNA digested with EcoRI, BamHI, and HindIII restriction enzymes.

Discussion

The involvement of a cyclin dependent kinase (cdk4), a cyclin (cyclin D1), and an inhibitor of cyclin-cdk complexes (p16) in human neoplasia and the localization of members of these gene families near chromosomal regions known to be involved in alterations in several human malignancies, as described herein, encourage speculation that one or more of these genes could similarly be candidates for contribution to oncogenic transformation. The gene for cdk3 was mapped to chromosome 17q22-qter telomeric to the BRCA1 locus. The possible involvement of cdk3 within reported regions of LOH telomeric to BRCA1 in breast cancer and a possible rearrangement of the gene was found in the MDA-MB-543 cell line was investigated. This rearrangement may result in the deregulation of cdk3 gene expression or in the production of an abnormal transcript. Alternatively, the rearrangement in the MDA-MB-543 cell line could result in a deletion encompassing a target gene in the region. Such a rearrangement with concurrent amplification of the ERBB2 gene was described in the BT474 breast cancer cell line. A deletion, possibly targeting the BRCA1 gene in this cell line was found to result in the expression of THRA1-BTR fusion transcripts (Futreal, P. A., et al., Cancer Res. 54:1791–17794, 1994). Thus, although a primary role for cdk3 in breast carcinogenesis is unlikely, it is possible that because of its putative oncogenic capacity, it is the target of secondary rearrangements which could have phenotypic consequences.

Cdk6 and PITALRE map to chromosomes 7p13-cen and 9q34.1, respectively. Both regions are involved in non-random chromosomal alterations. Deletions involving chromosome 7 at band p13 have been reported to be associated with non-Hodgkin's Lymphoma (NHL) where they probably represent a secondary chromosomal abnormality. T-cell NHL, on the other hand, have been reported to carry abnormalities involving chromosome 9 at band q34. Also, a t(8;9) translocation involving 9q34 has been observed in myeloproliferative disorders. Allelic losses at 9q34 have been reported in several malignancies. In particular, more than 40% of bladder tumors demonstrate LOH at 9q34.1–2. Both cdk6 and PITALRE are thought to be positive regulators of cell cycle progression and are therefore unlikely to be inactivated by deletions. The cdk6 gene may be near the EGFR region that is amplified or overexpressed in some tumors.

MDM2 expression, like that of the cyclin-cdk inhibitor, p21 at 6p21 is regulated by the p53 tumor suppressor and was reported to be one of the amplification targets at band 12q13 in human sarcomas. As mentioned previously, cdk4 and GLI are also included in the 12q13 ampiicon. The p27 gene was mapped to chromosome 12 at band p13. Chromosome 12 abnormalities have been reported in a significant number of CLL. More than twenty patient DNAs were tested by Southern blotting for abnormalities in the MDM2, cdk2, cdk4, and p27 genes. No evidence of rearrangement at the genomic level was found with any of the cDNA probes. Overexpression of MDM2 without evidence of DNA rearrangements was recently reported in CLL suggesting a role for this gene as a secondary mediator of transformation or tumor progression. The possibility of involvement of these genes in CLL through point mutations or rearrangements occurring outside the regions examined which could include regulatory sequences cannot be excluded. However, since gross alterations of the type known to result in oncogene activation do not appear to occur in a significant number of cases, it seems unlikely that any of these genes play a role as primary effectors of tumorigenesis in CLL. P27 may be active only in the presence of growth inhibitory extracellular signals, such as natural anti-mitogens and p27 activation may play a role in promoting stem cell differentiation. The possibility that p27, in concert with p15$^{INK4B}$, another recently cloned cdk inhibitor, is implicated in TGFβ arrested or contact inhibited cells, is currently under investigation using several leukemic cell lines. Additional chromosomal abnormalities which could the involve the p27 gene at 12p13 include isochromosomes of the short arm of chromosome 12 which constitute a characteristic abnormality in male germ cell tumors. More relevant to the possible involvement of a putative tumor suppressor, deletions of 12p13 have been observed in chronic lymphoproliferative disorders and deletions of 12p11-p13 have been observed in acute lymphoblastic and acute myeloblastic leukemia.

Finally, the gene for PISSLRE which maps to 16q24 is located in a region of reported LOH in breast, prostatic and other tumors. The predicted amino acid sequence of the PISSLRE protein shows highest homology (55% identity in the catalytic domain) to p58/GTA which has been shown to inhibit entry into S phase when over-expressed in CHO cells. Thus, although PISSLRE was cloned through homology to positive cell cycle regulators (the cdc2 family), it may actually function as a negative regulator of cell cycle progression. A loss or rearrangement of this gene in prostatic or breast carcinoma cell lines and tissue samples is currently under investigation, as well as the characterization of candidate interacting proteins that will help define its cell cycle contributions.

In summary, the genes for five proteins with putative roles in cell cycle control have been localized. Their chromosomal locations and proposed functions are consistent with possible involvement of some of these genes in the pathogenesis of human neoplasia.

Example 4

Gene constructs were made to test the effect of wild-type, antisense and phosphorylation-deficient mutants of PITALRE and PISSLRE on the phenotype of transformed cell lines. Gene constructs were made using pcDNA3 (Invitrogen Corp., San Diego) into which coding sequences were inserted, thereby placing them under the control of CMV promoter. Wild-type constructs of PITALRE and PISSLRE included SEQ ID NO:1 and SEQ ID NO:3, respectively, inserted into pcDNA3. Antisense constructs of PITALRE and PISSLRE included nucleotide sequences complementary to SEQ ID NO:1 and SEQ ID NO:3, respectively, inserted into pcDNA3. Phosphorylation deficient mutant constructs of PITALRE and PISSLRE included nucleotide sequences with modifications to SEQ ID NO:1 and SEQ ID NO:3, respectively, inserted into pcDNA3. Phosphorylation deficient mutants were generated by site directed mutagenesis to the consensus phosphorus transfer region. The consensus sequence KLADFGLAR (SEQ ID NO:5) is found in cdc2-related kinases and considered to be essential in the phospho-transfer reaction (See: van den Heuvel, S. and E. Harlow 1993 Science 262:2050–2054, which is incorporated herein by reference). The sequence is present as KLADFGLAR (SEQ ID NO:5) in PITALRE. The sequence is present as KTADFGLAR (SEQ ID NO:6) in PISSLRE. In phosphorylation deficient mutants, the D (aspattic acid) is replaced with an N (asparagine) and the phosphorylation activity of the protein is lost. SEQ ID NO:29 shows the amino acid sequence of the phosphorylation deficient PITALRE. SEQ ID NO:31 shows the amino acid sequence of the phosphorylation deficient PISSLRE. In phosphorylation deficient mutants, the D (aspartic acid) is replaced with an N (asparagine) and the phosphorylation activity of the protein is lost. As a control, pcDNA3 without insert was used as the seventh construct.

Co-transfection of each of the seven constructs was performed using 20 μg of construct DNA and 5 μg of CD20 expression construct. Co-transfection was carried out using standard protocols. CD20$^+$ cells were selected using standard techniques with anti-CD20 FITC antibodies and a cell sorter. CD20$^+$ were cultured 72 hours and stained. Foci were counted.

The data is shown in FIG. 1. Control is vector only (i.e. pcDNA-3 without insert). Wild-type PITALRE is the coding region of SEQ ID NO:1 in the recombinant vector pcDNA-3 under the control of the CMV promoter of the vector. Antisense PITALRE is the antisense sequence of the coding region of SEQ ID NO:1 in the recombinant vector pcDNA-3 under the control of the CMV promoter of the vector. Phosphorylation deficient PITALRE is a mutated form of the coding region of SEQ ID NO:1 such that SEQ ID NO:30 is produced. The coding sequence which encodes SEQ ID NO:30 is in the recombinant vector pcDNA-3 under the control of the CMV promoter of the vector. Wild-type PISSLRE is the coding region of SEQ ID NO:3 in the recombinant vector pcDNA-3 under the control of the CMV promoter of the vector. Antisense PISSLRE is the antisense sequence of the coding region of SEQ ID NO:3 in the recombinant vector pcDNA-3 under the control of the CMV promoter of the vector. Phosphorylation deficient PISSLRE is a mutated form of the coding region of SEQ ID NO:3 such that SEQ ID NO:31 is produced. The coding sequence which endcodes SEQ ID NO:31 is in the recombinant vector pcDNA-3 under the control of the CMV promoter of the vector.

The data clearly indicate that the presence of either the antisense transcript or phosphorylation deficient PITALRE or PISSALRE blocks progress of the cells through $G_2/M$. The presence of antisense also inhibited the progress of the cells through the $G_2/M$ phase of the cell cycle. By blocking the progress of the cells through the cell cycle, cell division and, thus, cell proliferation is prevented.

Example 5

PITALRE immunocomplexes may be isolated from frozen cells. HeLa cells are useful for isolating PITALRE immunocomplexes. The following is an immunoprecipitation protocol for isolating the immunocomplexes 1. Thaw out 1 pellet of frozen cells.

2. Add 0.5–1 ml lysis buffer* per pellet and incubate 30 min in ice.

3. a) Spin down 10 min. Transfer supernatant to a fresh tube, add 40 μl/pellet of Normal Rabbit Sera and incubate 30 min in ice.

b) Thaw out 1 pellet (1 ml) of frozen SAC (*Staphylococcus aureus* Colan) (Zysorbin 100 ml, Zymed) and keep it in ice until it sediments.
   Spin down 20–30 sec.
   Resuspend in 1 ml of lysis buffer.
   Spin down 10–30 sec.

5. Resuspend the SAC pellet with the NRbS-blocked cell lysate, and incubate 30 min in ice.

6. Spin down 10 min. Carefully transfer the precleared supernatant without taking any SAC (spin down again and repeat if necessary).

7. Split the precleared lysate into aliquots (100–300 μl).
8. Add the primary antibody (α PITALRE 5–10 μg)
9. Add 30–40 μl of Protein A-Sepharose (Pierce, Ref. 20334), and rock for 1 hour at 4° C.
10. Spin down 5–10 sec, and resuspend in 1 ml of lysis buffer, vortex briefly.
11. Repeat step 9 twice.
12. Spin down 5–10 sec, aspirate and add Laemmli's Sample Buffer 30–40. Boil the samples 3 min and spin them down. The samples are now ready for SDS/PAGE.

*Lysis buffer:

50 mM Tris-Cl pH 7.4 25 ml of 1M 5 mM EDTA 5 ml of 0.5M 250 mM NaCl 25 ml of 5M 50 mM NaF 50 ml of 0.5M 0.1% Triton X-100 0.5 ml 0.1 mM $Na_3VO_4$ 0.5 ml of 0.1M $H_2O$ 394 ml (store at 4° C.)
For immediate use:
Lysis buffer stock 50 ml
1 mM PMSG (1 aliquot) 0.5 ml of 100 mM
10 μg/ml leupeptin (1 aliquot) 50 μl of 10 mg/ml
*Rabbit anti-IgG:Cappel, Ref. 55480

Example 6

In vitro assays to detect phosphorylation by isolated PITALRE immunocomplexes are performed by as follows.

1. Perform an immunoprecipitation as described in the immunoprecipitation protocol above except step 12 is not followed. For some antibodies it is convenient to perform additional preclearing, i.e.:

2 additional SAC preclearing steps (30 min).
1–2 incubations with PAS, 100 μl/pellet (45 min to O/N).

2. Once the immunoprecipitation is completed up to step 11 as described above, the protein-A-sepharose beads containing the immunocomplexes are washed once with kinase buffer (20mMHEPES pH 7.4, 10mMMgAc-). The material is then spun down 5–10 sec, aspirate and the pellet is used in the kinase assay as follows.

3. Reaction buffer will depend on the protein kinases present in the immunocomplexes. For example:

add to the washed beads (the pellet)
5 μl of substrate (1 μg).
20 μl of reaction buffer and mix by short vortex.
incubate 30 min at 30° C.
stop the reaction by adding 2× Laemmli sample buffer.
load a SDS polyacrylamide gel.
Reaction Buffer (prepared on ice):
2.5×a μl 10× kinase Assay Buffer (KAS)
(17.5×a)- a μl $H_2O$
a/2 μl γ-$^{32}$P-ATP (last step, just before starting the reaction)
10× Kinase Assay Buffer (KAS):
200 mM HEPES pH 7.4
100 mM MgAc
200 μM ATP
10 mM DTT
γ-$^{32}$P-ATP from Dupont 3000 Ci/mmol, 10 mCi/ml, 6.66 10$^6$ cpm/pmol (NEG-002A).

---

I claim:

1. An isolated nucleic acid molecule consisting of SEQ ID NO:1, SEQ ID NO:3, or a fragment thereof having at least 18 nucleotides.

2. The nucleic acid molecule of claim 1 consisting of a fragment of SEQ ID NO:1 or SEQ ID NO:3 having at least 18 nucleotides.

3. The nucleic acid molecule of claim 1 consisting of a fragment of SEQ ID NO:1 or SEQ ID NO:3 having 18–30 nucleotides.

4. The nucleic acid molecule of claim 1 consisting of a fragment of SEQ ID NO:1 or SEQ ID NO:3 having 24 nucleotides.

5. An isolated nucleic acid molecule consisting of SEQ ID NO:1 or SEQ ID NO:3.

6. The nucleic acid molecule of claim 5 consisting of SEQ ID NO:1.

7. The nucleic acid molecule of claim 5 consisting of SEQ ID NO:3.

8. A recombinant expression vector comprising the nucleic acid molecule of claim 5.

9. A host cell comprising the recombinant expression vector of claim 8.

10. A recombinant expression vector comprising a nucleic acid sequence that encodes a protein having the amino acid sequence of SEQ ID NO:2 or SEQ ID NO:4.

11. A host cell comprising the recombinant expression vector of claim 10.

* * * * *

UNITED STATES PATENT AND TRADEMARK OFFICE
CERTIFICATE OF CORRECTION

PATENT NO. : 5,674,748
DATED : October 7, 1997
INVENTOR(S) : Antonio Giordano

It is certified that error appears in the above-indentified patent and that said Letters Patent is hereby corrected as shown below:

Col. 3, line 19, there should be a space between "foranti-cancer" --for anti-cancer--.

Col. 17, line 44, after "sonication" the word "insoluble" should be initial capital --I--.

Col. 18, line 16, "CDKS" should be --CDK5--.

Col. 18, line 67, "~50bp" should be --~450 bp--.

Col. 20, line 55, "GS" should be --G8--.

Col. 24, line 54, "ampiicon" should be --amplicon--.

Signed and Sealed this

Twentieth Day of January, 1998

BRUCE LEHMAN

Attest:

Attesting Officer

Commissioner of Patents and Trademarks